(12) United States Patent
Bryant et al.

(10) Patent No.: US 7,749,730 B2
(45) Date of Patent: Jul. 6, 2010

(54) HIGH THROUGHPUT SCREENING ASSAY FOR THE TRPM5 ION CHANNEL

(75) Inventors: Robert W. Bryant, Princeton, NJ (US); S. Paul Lee, Newtown, PA (US); R. Kyle Palmer, Cranbury, NJ (US); Qifeng Yang, Belle Meade, NJ (US); M. N. Tulu Buber, Newtown, PA (US)

(73) Assignee: Redpoint Bio Corporation, Ewing, NJ (US)

( * ) Notice: Subject to any disclaimer, the term of this patent is extended or adjusted under 35 U.S.C. 154(b) by 251 days.

(21) Appl. No.: 11/592,180

(22) Filed: Nov. 3, 2006

(65) Prior Publication Data

US 2007/0111264 A1    May 17, 2007

Related U.S. Application Data

(60) Provisional application No. 60/732,636, filed on Nov. 3, 2005.

(51) Int. Cl.
    *C12P 1/00*    (2006.01)
(52) U.S. Cl. .......................................... 435/41
(58) Field of Classification Search .................. 435/7.1, 435/7.2, 7.91, 7.92
    See application file for complete search history.

(56) References Cited

U.S. PATENT DOCUMENTS

| | | | |
|---|---|---|---|
| 4,399,216 A | 8/1983 | Axel et al. | |
| 5,010,175 A | 4/1991 | Rutter et al. | |
| 5,288,514 A | 2/1994 | Ellman | |
| 5,506,107 A | 4/1996 | Cunninghman et al. | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,569,588 A | 10/1996 | Ashby et al. | |
| 5,580,748 A * | 12/1996 | Alkon et al. | 435/29 |
| 5,593,853 A | 1/1997 | Chen et al. | |
| 5,876,946 A * | 3/1999 | Burbaum et al. | 435/7.1 |
| 6,188,965 B1 | 2/2001 | Mayo et al. | |
| 6,296,312 B1 | 10/2001 | Congleton et al. | |
| 6,403,312 B1 | 6/2002 | Dahiyat et al. | |
| 6,641,997 B1 * | 11/2003 | MacKinnon | 435/6 |
| 7,135,298 B2 * | 11/2006 | Abraham | 435/7.1 |
| 2004/0072254 A1 | 4/2004 | Callamaras et al. | |
| 2004/0259160 A1 * | 12/2004 | Johnson et al. | 435/7.1 |
| 2005/0019830 A1 | 1/2005 | Penner et al. | |
| 2007/0004680 A1 * | 1/2007 | Babinski et al. | 514/81 |
| 2007/0161052 A1 | 7/2007 | Servant et al. | |

FOREIGN PATENT DOCUMENTS

| | | |
|---|---|---|
| WO | WO 91/19735 A1 | 12/1991 |
| WO | WO 92/00091 A1 | 1/1992 |
| WO | WO 93/09222 A2 | 5/1993 |
| WO | WO 93/20242 A1 | 10/1993 |
| WO | WO 94/12650 A2 | 6/1994 |
| WO | WO 95/31560 A1 | 11/1995 |
| WO | WO 97/00271 A1 | 1/1997 |
| WO | WO 01/25277 A1 | 4/2001 |

OTHER PUBLICATIONS

Mertz et al. (Am. J. Physiology: cell physiology 1990 vol. 258, p. C654-C661).*
Prawitt et al. (PNAS 2003 vol. 100, p. 15166-15171).*
Avenet, P., and Lindemann, B., "Perspective of Taste Reception," *J. Membrane Biol. 112*:1-8, Springer-Verlag New York Inc. (1989).
Baxter, D.F., et al., "A Novel Membrane Potential-Sensitive Fluorescent Dye Improves Cell-Based Assays for Ion Channels," *J. Biomol. Screen. 7*:79-85, The Society for Biomolecular Screening (2002).
Behrendt, H.-J., et al., "Characterization of the mouse cold-menthol receptor TRPM8 and vanilloid receptor type-1 VR1 using a fluorometric imaging plate reader (FLIPR) assay," *Br. J. Pharmacol. 141*:737-745, Nature Publishing Group (Feb. 2004).
Campbell, D.A., and Bermak, J.C., "Phosphonate Ester Synthesis Using a Modified Mitsunobu Condensation," *J. Org. Chem. 59*:658-660, American Chemical Society (1994).
Chen, C., et al., ""Analogous" Organic Synthesis of Small-Compound Libraries: Validation of Combinatorial Chemistry in Small-Molecule Synthesis," *J. Am. Chem. Soc. 116*:2661-2662, American Chemical Society (1994).
Cho, C.Y., et al., "An Unnatural Biopolymer," *Science 261*:1303-1305, American Association for the Advancement of Science (1993).
DeWitt, S.H., et al., ""Diversomers": An approach to nonpeptide, nonoligomeric chemical activity," *Proc. Natl. Acad. Sci. USA 90*:6909-6913, National Academy of Sciences (1993).
Epps, D. E., et al., "Characterization of the steady-state and dynamic fluorescence properties of the potential-sensitive dye bis-(1,3-dibutylbarbituric acid)trimethine oxonol (Dibac$_4$(3)) in model systems and cells," *Chem. Phys. Lipids 69*:137-150, Elsevier Science Ireland Ltd. (1994).
Furka, Á., et al., "General method for rapid synthesis of multicomponent peptide mixtures," *Int. J. Pept. Prot. Res. 37*:487-493, Munksgaard International Publishers (1991).
Gossen, M., and Bujard, H., "Tight control of gene expression in mammalian cells by tetracycline-responsive promoters," *Proc. Natl. Acad. Sci. USA 89*:5547-5551, National Academy of Sciences (1992).
Hagihara, M., et al., "Vinylogous Polypeptides: An Alternative Peptide Backbone," *J. Am. Chem. Soc. USA 114*:6568-6570, American Chemical Society (1992).

(Continued)

*Primary Examiner*—Jacob Cheu
(74) *Attorney, Agent, or Firm*—Sterne, Kessler, Goldstein & Fox P.L.L.C.

(57) ABSTRACT

There exists a need in the art for high throughput screening assays that can identify compounds that specifically modulate the activity of fast-acting ion channels, such as TRPM5. Current methods suffer from a lack of sensitivity, low throughput, and are labor intensive. The claimed methods provide fluorescent assays with an optical readout that gives rapid readout of the results, has a high signal to noise background ratio, are easy to use, can be modified for automation and miniaturization, and provide verification that a compound specifically modulates TRPM5.

17 Claims, 17 Drawing Sheets

OTHER PUBLICATIONS

Hamill, O.P., and Sakmann, B., "Multiple conductance states of single acetylcholine receptor channels in embryonic muscle cells," *Nature 294*:462-464, Macmillan Journals Ltd. (1981).

Hirschmann, R., et al., "Nonpeptidal Peptidomimetics with a β-D-Glucose Scaffolding. A Partial Somatostatin Agonist Bearing a Close Structural Relationship to a Potent, Selective Substance P Antagonist," *J. Am. Chem. Soc. 114*:9217-9218, American Chemical Society (1992).

Hofmann, T., et al., "TRPM5 Is a Voltage-Modulated and $Ca^{2+}$-Activated Monovalent Selective Cation Channel," *Curr. Biol. 13*:1153-1158, Elsevier Science Ltd. (2003).

Houghten, R.A., et al., "Generation and use of synthetic peptide combinatorial libraries for basic research and drug discovery," *Nature 354*:84-86, Nature Publishing Group (1991).

Kewon, W.A., et al., "Methods for Introducing DNA into Mammalian Cells," *Meth. Enzym. 185*:527-537, Academic Press (1990).

Kinnamon, S.C., "Taste transduction: a diversity of mechanisms," *TINS 11*:491-496, Elsevier Publications, Cambridge (1998).

Liang, R., et al., "Parallel Synthesis and Screening of a Solid Phase Carbohydrate Library," *Science 274*:1520-1522, American Association for the Advancement of Science (1996).

Mansour, S.L., et al., "Disruption of the proto-oncogene int-2 in mouse embryo-derived stem cells: a general strategy for targeting mutations to non-selectable genes," *Nature 336*:348-352, Nature Publishing Group (1988).

Margolskee, R.F., "Molecular Mechanisms of Bitter and Sweet Taste Transduction," *J. Biol. Chem. 277*:1-4, The American Society for Biochemistry and Molecular Biology, Inc. (2002).

Misteli, T., and Spector, D.L., "Applications of the green fluorescent protein in cell biology and biotechnology," *Nat. Biotechnol. 15*:961-964, Nature Publishing Group (1997).

Mojet, J., et al., "Taste Perception with Age: Generic or Specific Losses in Threshold Sensitivity to the Five Basic Tastes?" *Chem. Senses 26*:845-860, Oxford University Press (2001).

Park, K.-S., et al., "Phenotypic alteration of eukaryotic cells using randomized libraries of artificial transcription factors," *Nat. Biotech. 21*:1208-1214, Nature Publishing Group (2003).

Pérez,C.A., et al., "A transient receptor potential channel expressed in taste receptor cells," *Nat. Neurosci. 5*:1169-1176, Nature Publishing Group (2002).

Prawitt, D., et al., "Identification and characterization of *MTR1*, a novel gene with homology to melastatin (*MLSN1*) and the *trp* gene family located in the BWS-WT2 critical region on chromosome 11p15.5 and showing allele-specific expression," *Hum. Mol. Gen. 9*:203-216, Oxford University Press (2000).

Vaughan, T.J., et al., "Human Antibodies with Sub-nanomolar Affinities Isolated from a Larger Non-immunized Phage Display Library," *Nat. Biotechnol. 14*:309-314, Nature Publishing Group (1996).

Whiteaker, K.L., et al., "Validation of FLIPR Membrane Potential Dye for High Throughput Screening of Potassium Channel Modulators," *J. Biomol. Screen. 6*:305-312, The Society for Biomolecular Screening (2001).

Zhang, J.-H., et al., "A Simple Statistical Parameter for Use in Evaluation and Validation of High Throughput Screening Assays," *J. Biomol. Screen. 4*:67-73, Society for Bimolecular Screening (1999).

Zhang, Y., et al., "Coding of Sweet, Bitter, and Umami Tastes: Different Receptor Cells Sharing Similar Signaling Pathways," *Cell 112*:293-301, Cell Press (2003).

Zochowski, M., et al., "Imaging Membrane Potential with Voltage-Sensitive Dyes," *Biol. Bull. 198*:1-21, Marine Biological Laboratory (2000).

GenBank Accession No. AY280364, Hoffman et al., (Jul. 22, 2003).
GenBank Accession No. AY280365, Hoffman et al., (Jul. 22, 2003).
GenBank Accession No. AAP44476, Hoffman et al., (Jul. 22, 2003).
GenBank Accession No. AAP44477, Hoffman et al., (Jul. 22, 2003).
GenBank Accession No. NP_055370, Liman (Sep. 3, 2007).
GenBank Accession No. NM_014555, Liman (Sep. 3, 2007).
GenBank Accession No. NP_064673, Zhang et al., (Sep. 30, 2007).
GenBank Accession No. NM_020277, Zhang et al., (Sep. 30, 2007).

* cited by examiner

Generation of the TRPM5 FLIPR Response in Transfected CHO Cells

High and Low Controls for HTS TRPM5 Assay

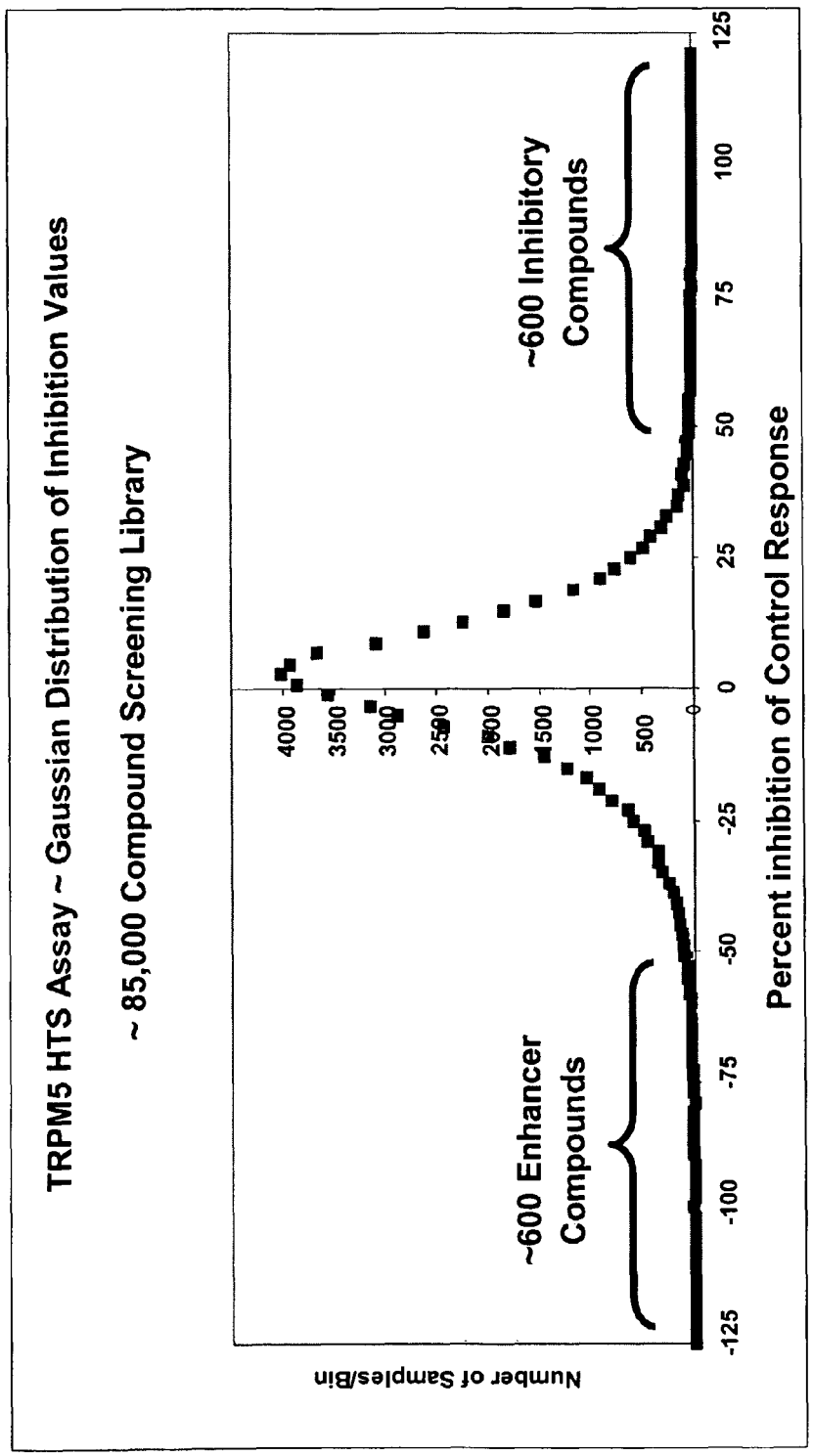
FIG. 6 Results from a TRPM5 high throughput screen (HTS) on >85K compounds.

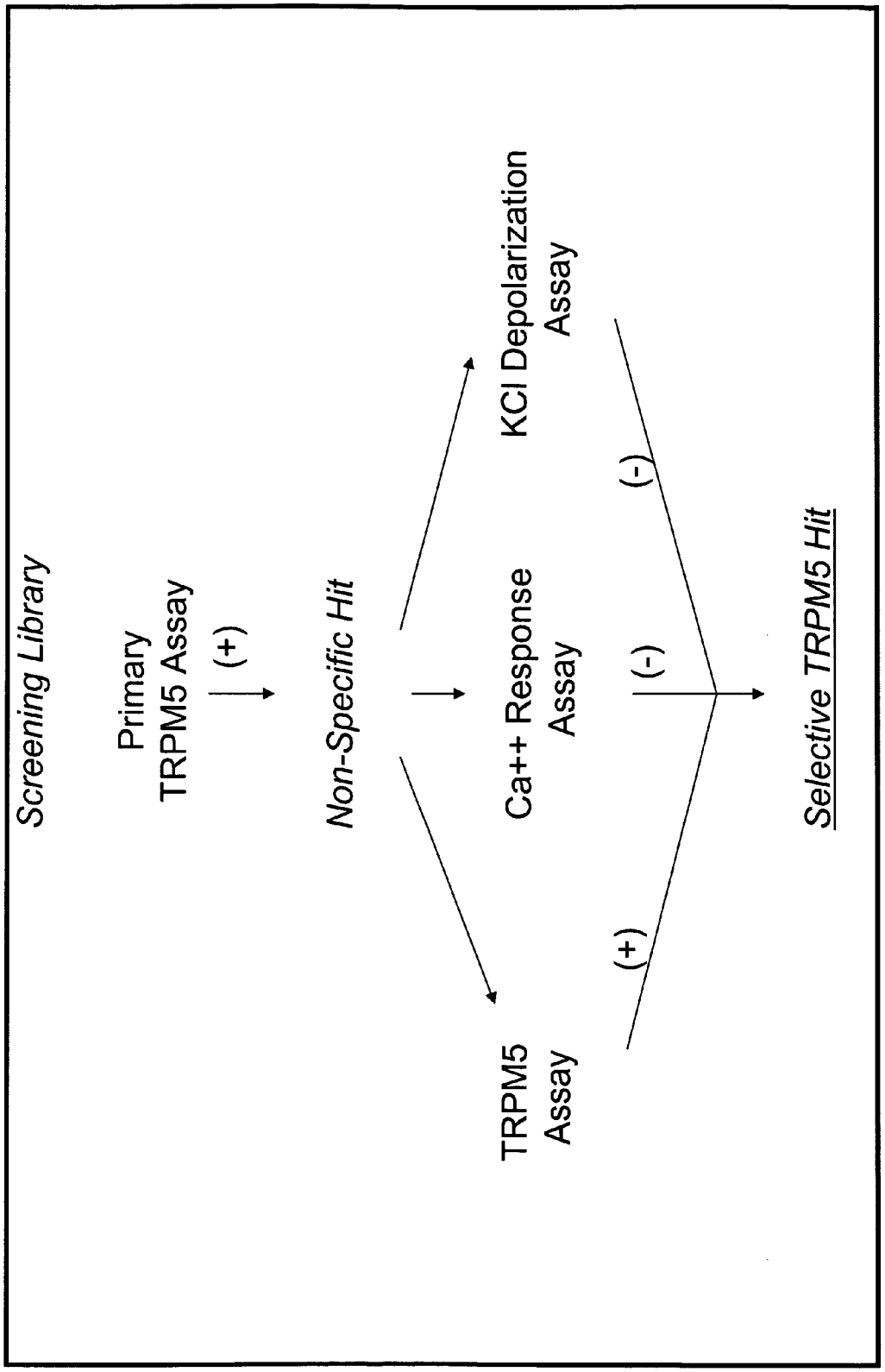

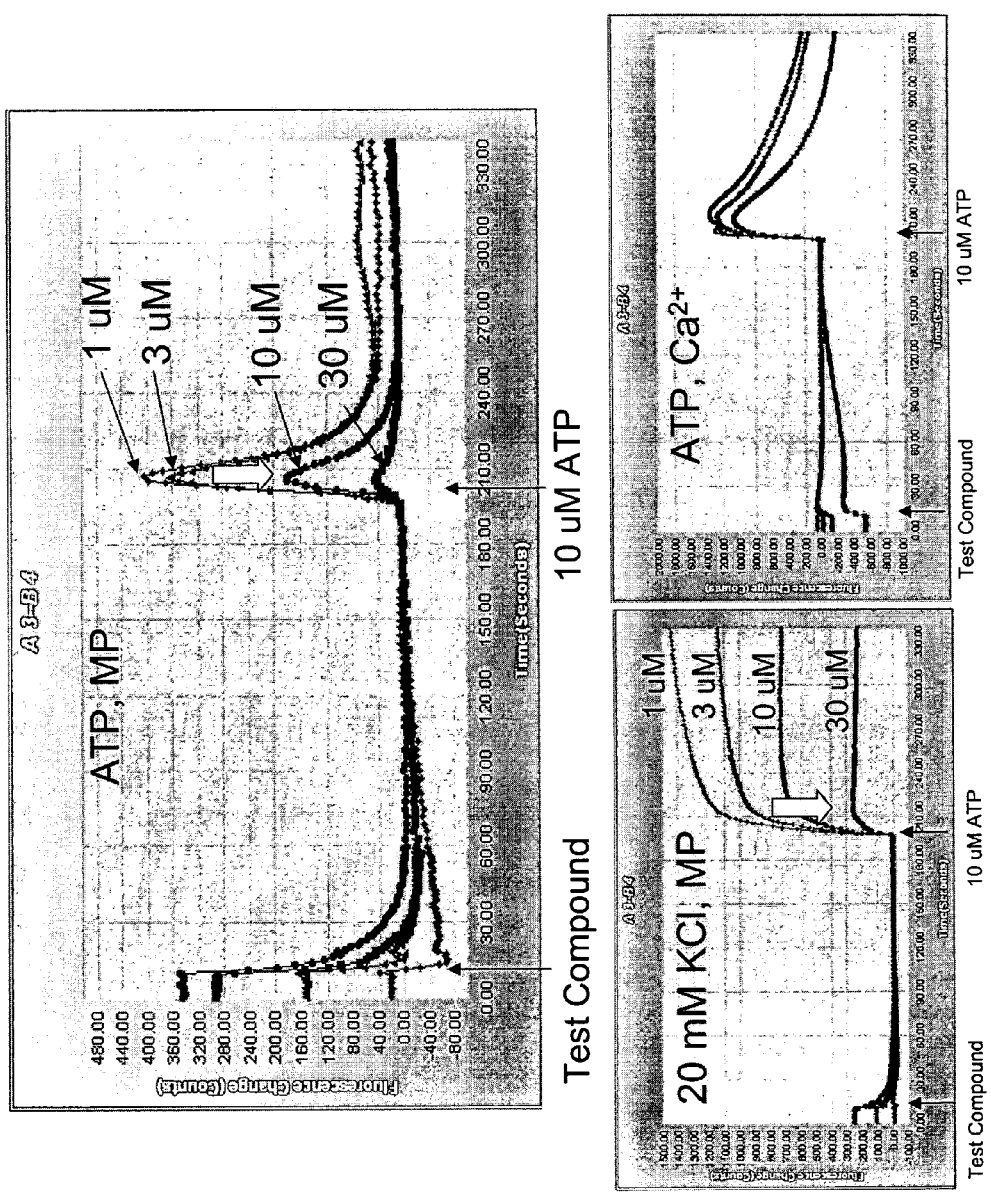
FIG. 8A: Compound F001344, A3 inhibits (↓) signal of TRPM5 AND KCl Assays

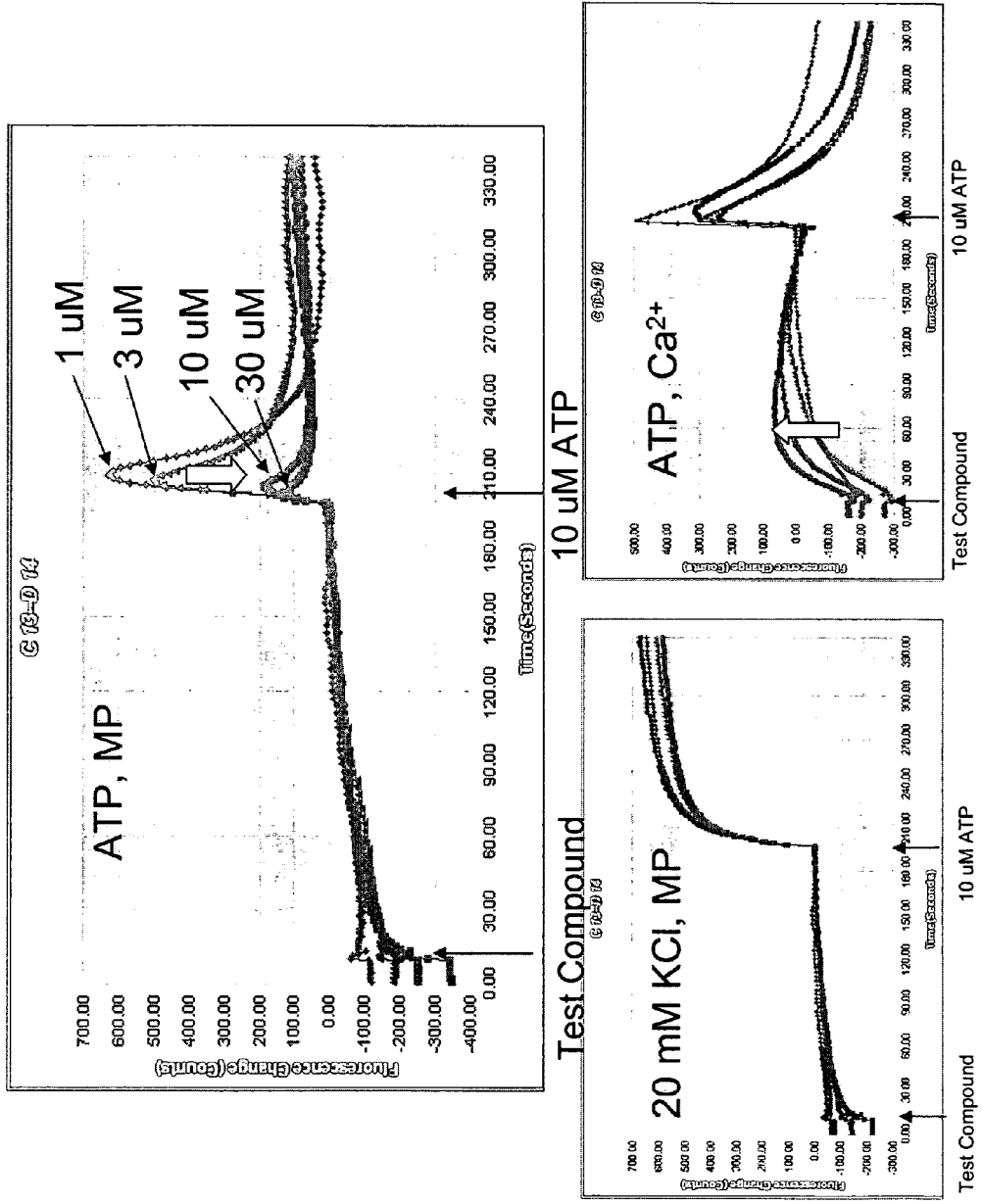
FIG. 8B: Compound F001348, C13 inhibits TRPM5 signal but activates Ca++ signal KCl Counterscreen for Discovery of TRPM5 Specific Inhibitors: FLIPR Traces Demonstrating a "Clean" TRPM5 Inhibitor, Compound 1 : No KCl or Ca++ Flux Activity Dose Responsive Inhibition of TRPM5 by Compound 1
Without Inhibiting KCl Depolarization or Inhibition of Ca$^{++}$ Flux Activation

Figure 9C
Examples of Non-Specific Inhibition of TRPM5
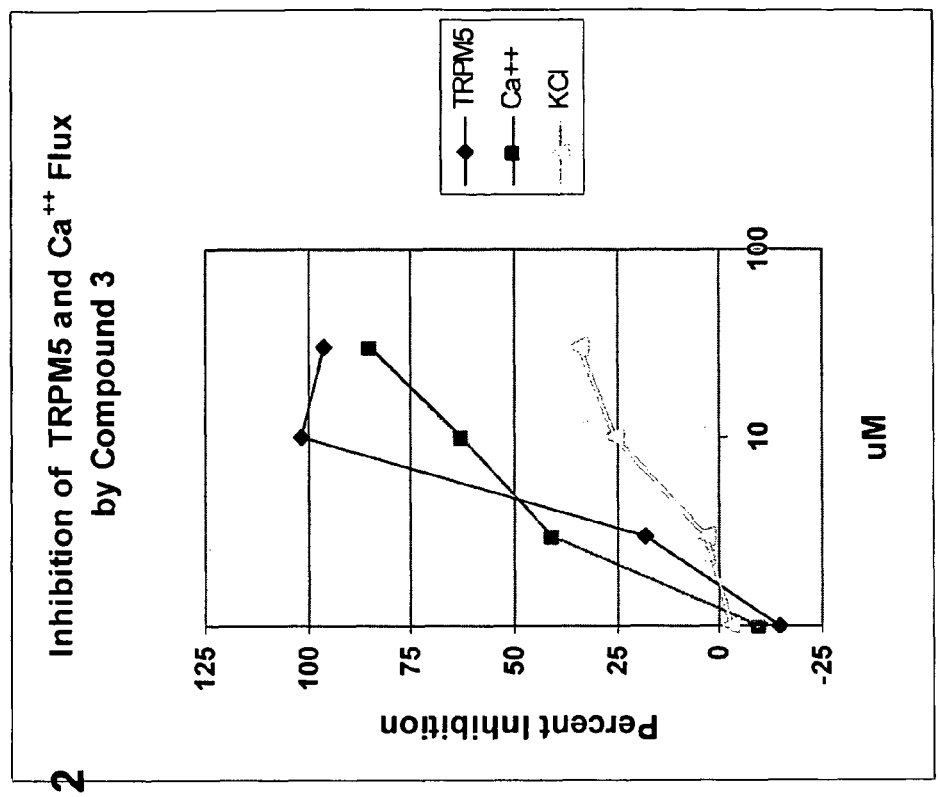
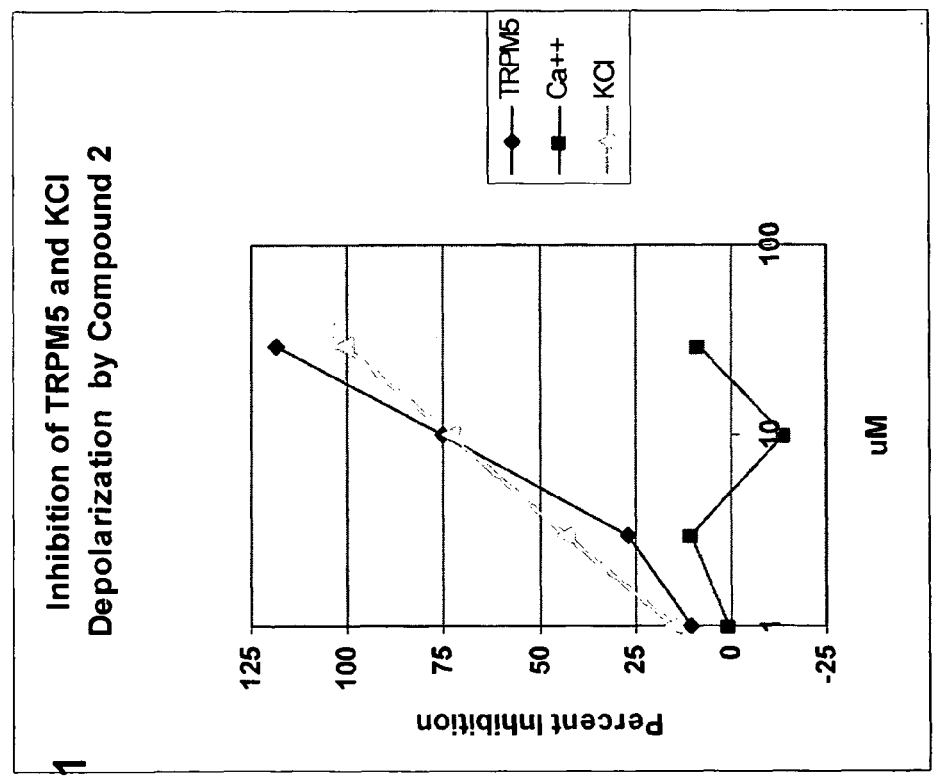

Compound 4: A Selective TRPM5 Enhancer

Dose Responsive Stimulation of TRPM5 Activity by Compound 4

Demonstration that Compound 5 Selectively Enhances TRPM5 Activity at Sub-Optimal Concentration of the GPCR Agonist ATP TRPM5 (Membrane Potential) response to A23187

TRPM5 (Membrane Potential) response to Carbachol

HIGH THROUGHPUT SCREENING ASSAY FOR THE TRPM5 ION CHANNEL

CROSS REFERENCE TO RELATED APPLICATIONS

This application claims the benefit of U.S. Prov. Appl. No. 60/732,636, filed Nov. 3, 2005, which is herein incorporated by reference.

BACKGROUND OF THE INVENTION

1. Field of the Invention

The present invention is related to a high throughput screening method for compounds that impact taste. More specifically, the present invention relates to a screening method useful in the identification of compounds that affect taste sensation by modulating the activity of the ion channel TRPM5. The screening method, using fluorescent membrane potential dyes, allows for the rapid screening of thousands of compounds by providing a visual fluorescent readout that can be easily automated.

2. Background

Taste perception not only plays a critical role in the nutritional status of human beings, but is also essential for the survival of both lower and higher animals (Margolskee, R. F. *J. Biol. Chem.* 277:1-4 (2002); Avenet, P. and Lindemann, B. *J. Membrane Biol.* 112:1-8 (1989)). Taste perception is carried out by taste receptor cells (TRCs). TRCs perceive the multitude of compounds that are associated with a given taste, and convert that perception to a signal deciphered by the brain, resulting in sweet, bitter, sour, salty, or umami (savory) taste.

TRCs are polarized epithelial cells, meaning they have specialized apical and basolateral membranes. Taste buds contain 60-100 TRCs, each having a tiny portion of its membrane exposed on the mucosal surface of the tongue (Kinnamon, S. C. *TINS* 11:491-496 (1988)). Sensory transduction is initiated by sapid molecules, or "tastants," that interact with microvillar processes on the apical membrane of TRCs. The tastants bind specific membrane receptors, leading to a voltage change across the cell membrane; in turn this depolarizes, or changes the electric potential of the cell, causing transmitter release and excitation of primary gustatory nerve fibers.

Ion channels are transmembrane proteins that form pores in a membrane and allow ions to pass from one side to the other (reviewed in B. Hille (Ed), 1992, Ionic Channels of Excitable Membranes 2nd ed., Sinauer, Sunderland, Mass.). Although certain ion channels are open under all physiological membrane conditions (so-called leaky channels), many channels have "gates" that open in response to a specific stimulus. As examples, voltage-gated channels respond to a change in the electric potential across the membrane, mechanically-gated channels respond to mechanical stimulation of the membrane, and ligand-gated channels respond to the binding of specific molecules. Various ligand-gated channels can open in response to extracellular factors, such as a neurotransmitters (transmitter-gated channels), or intracellular factors, such as ions (ion-gated channels), or nucleotides (nucleotide-gated channels). Still other ion channels are modulated by interactions with proteins, such as G-proteins (G-protein coupled receptors or GPCRs).

Most ion channel proteins mediate the permeation of one predominant ionic species. For example, sodium ($Na^+$), potassium ($K^+$), chloride ($Cl^-$), and calcium ($Ca^{2+}$) channels have been identified.

One recently discovered ion channel, TRPM5, has been shown to be essential for taste transduction. Perez et al., *Nature Neuroscience* 5:1169-1176 (2002); Zhang et al., *Cell* 112:293-301 (2003). TRPM5 is a member of the transient receptor potential (TRP) family of ion channels. TRPM5 forms a channel through the membrane of the taste receptor cell, and is believed to be activated by stimulation of a receptor pathway coupled to phospholipase C and by $IP_3$-mediated $Ca^{2+}$ release. The opening of this channel is dependent on a rise in $Ca^{2+}$ levels. Hofmann et al., *Current Biol.* 13:1153-1158 (2003). The activation of this channel leads to depolarization of the TRC, which in turn leads to transmitter release and excitation of primary gustatory nerve fibers.

Because TRPM5 is a necessary part of the taste-perception machinery, its inhibition prevents an animal from sensing particular tastes. Although taste perception is a vital function, the inhibition, or masking, of undesirable tastes is beneficial under certain circumstances. For example, many active pharmaceutical ingredients of medicines produce undesirable tastes, such as a bitter taste. Inhibition of the bitter taste produced by the medicine may lead to improved acceptance by the patient. In other circumstances, enhancement of taste may be desirable as in the case of developing improved artificial sweeteners or in treatment of taste losses in groups such as the elderly. Mojet et al., *Chem Senses* 26:845-60 (2001).

TRPM5 displays voltage modulation and rapid activation/deactivation ("opening and closing") kinetics upon receptor stimulation (Hofmann et al. 2003) which allows for the passage of monovalent cations, such as sodium and potassium. A closely related protein, TRPM4b, also shows $Ca^{2+}$ dependent voltage modulation, but opens and closes much slower than TRPM5. Thus, TRPM5 is the first example of a voltage-modulated, Ca2+-activated, monovalent cation channel that has rapid activation/deactivation kinetics (Hofmann et al. 2003).

Ion channel activation or inhibition may be determined by measuring changes in cell membrane potential when cells are exposed to certain stimuli. This is an indirect method of evaluating ion channel modulation, as cell membrane potential may be affected by multiple channels.

One method for testing ion channel activity is to measure changes in cell membrane potential using the patch-clamp technique. (Hamill et al., *Nature* 294:462-4 (1981)). In this technique, a cell is attached to an electrode containing a micropipette tip which directly measures the electrical conditions of the cell. This allows detailed biophysical characterization of changes in membrane potential in response to various stimuli. Thus, the patch-clamp technique can be used as a screening tool to identify compounds that modulate activity of ion channels. However, this technique is difficult to master and requires significant expertise to generate consistent, reliable data. Moreover, this technique is time consuming and would allow fewer than two or three compounds per day to be screened for activity.

Ideally, methods of screening test compounds are high throughput (i.e., allow for many compounds to be screened quickly), automated, easy to use, sensitive, and selective. Screening assays should also provide a high signal to background noise ratio. (Baxter et al., *J. Biomol. Screen.* 7:79-85 (2002)). Background noise is the minimal stimulation that a compound produces regardless of its effect on the ion channel. The high ratio makes visualization of positive or negative modulators simpler because the smallest response will be seen over the background measurements. This leads to a clear identification of modulating compounds.

A potential high throughput method for determining ion channel modulation utilizes fluorescent dyes that produce a fluorescent signal when the cell membrane potential changes. Increases in fluorescence occur, because upon a change in the membrane potential, the fluorescent dyes "flip" their orientation in the cell membrane bilayer from an intracellular to extracellular location. This flip causes an increase in fluorescence that is easily detected and quantified usually using an optical reader. Optical readouts of ion channel function are favorable for high throughput screening because they are potentially sensitive, versatile, and amenable to miniaturization and automation. Present day optical readers detect fluorescence from multiple samples in a short time and can be automated. Fluorescence readouts are used widely both to monitor intracellular ion concentrations and to measure membrane potentials.

In an attempt to overcome some of the shortcomings of traditional fluorescent dyes, modified bisoxonol fluorescent dyes such as the FLIPR® Membrane Potential dyes (FMP) from Molecular Devices were developed.

FMP dyes have been effective in correlating fluorescence with membrane potential determined directly by patch-clamp recording for "slow" ion channels (Baxter et al., *J. Biomol. Screen.* 7:79-85 (2002); Behrendt et al., *British J. Pharmacol.* 141:737-745 (2004); and Whiteaker et al., *J. Biomol. Screen.* 6:305-312 (2001).

A major challenge in designing a high throughput screening (HTS) method for compounds that modulate a specific ion channel is that methods of determining channel activation are indirect. To identify compounds that affect taste through modulation of TRPM5 activity, there must be a demonstration that the effect of the compounds on taste is specific to TRPM5 and not also to one or more of the multitude of other channels and receptors located on the cell surface. Additionally, since TRPM5 activation is calcium dependent, specificity of the TRPM5/test compound interaction must be confirmed by excluding those compounds that also modulate GPCR-agonist calcium flux.

Therefore, there exists a need in the art for HTS assays that can distinguish compounds that modulate taste by specifically acting on TRPM5, from compounds that may act by other mechanisms and that may not affect taste perception. The claimed invention provides HTS methods that give rapid and specific results, have a high signal to background ratio, and are easy to use.

BRIEF SUMMARY OF THE INVENTION

A new high throughput screening assay has been discovered that allows for the rapid screening of compounds that modulate TRPM5 ion channel activity. The method of the invention is more selective than methods that rely only on evaluation of a change in membrane potential. The invention will allow a practitioner to distinguish agents that are non-specific modulators of ion channels from agents that act via modulation of TRPM5. Moreover, the method will allow thousands of compounds that potentially modulate this fast ion channel, and affect taste, to be screened quickly and reliably.

An embodiment of the present invention is a high throughput screening assay for screening potential enhancers of the TRPM5 ion channel comprising contacting a cell expressing TRPM5 with a suboptimal concentration of an agent that increases intracellular calcium concentration, wherein the cell has been preloaded with a membrane potential fluorescent dye; contacting said cell with a potential enhancing compound; using an optical detector, measuring the fluorescent intensity of said cell in the presence of said potential enhancing compound; and comparing the measured fluorescent intensity to the fluorescent intensity of a different cell expressing TRPM5 in the presence of an optimal concentration of an agent that increases intracellular calcium concentration.

An additional embodiment of the invention is a high throughput screening assay for determining whether a test compound is a TRPM5 ion channel-specific modulator comprising contacting a cell that expresses TRPM5 and has been preloaded with a membrane potential fluorescent dye, with a test compound in the presence of potassium chloride; using an optical detector, measuring the fluorescent intensity of said cell in the presence of said potential modulating compound; comparing the measured fluorescent intensity determined above to the fluorescent intensity of a different cell that expresses TRPM5 and has been preloaded with a membrane potential dye in the presence of potassium chloride and the absence of the test compound; and evaluating whether the test compound may be a TRPM5-specific modulator by determining if the ratio of the fluorescent intensity with KCl and the test compound to the intensity with KCl in the absence of the test compound is less than or greater than 1.

An additional embodiment of the invention is a high throughput screening assay for determining whether a test compound is a TRPM5 ion channel-specific modulator comprising contacting a cell that expresses TRPM5 and has been preloaded with an intracellular calcium dye, with a test compound and a suboptimal concentration of a calcium modulating agent that increases intracellular calcium concentration; using an optical detector, measuring the fluorescent intensity of said cell in the presence of said calcium modulating compound; comparing the measured fluorescent intensity determined above to the fluorescent intensity of a different cell that expresses TRPM5 and has been preloaded with an intracellular calcium dye, in the presence of a suboptimal concentration of a calcium modulating agent and the absence of the test compound; and evaluating whether the test compound may be a TRPM5-specific modulator by determining if the ratio of the fluorescent intensity with a suboptimal concentration of a calcium modulating agent and the test compound, to the intensity with a suboptimal concentration of a calcium modulating agent in the absence of the test compound is less than or greater than 1.

Another embodiment of the claimed invention is a high throughput screening assay for screening potential enhancers of the TRPM5 ion channel comprising contacting a cell expressing both wildtype TRPM5 and a nonfunctional TRPM5 and has been preloaded with a membrane potential fluorescent dye, with a potential enhancer in the presence of an agent that increases the calcium concentration in said cell; using an optical detector, measuring the fluorescent intensity of said cell in the presence of said potential enhancer; and comparing the measured fluorescent intensity determined above to the fluorescent intensity of a cell that expresses wildtype TRPM5 and that has been preloaded with a membrane potential dye, in the presence of the potential enhancing compound to determine the extent of TRPM5 enhancement.

In some embodiments, the nonfunctional TRPM5 contains a deletion of the first 1000 base pairs of the TRPM5 gene. In another embodiment, the nonfunctional TRPM5 contains a deletion of the first 2000 base pairs of the TRPM5 gene.

In some embodiments, the claimed method further comprises selecting a compound that enhances TRPM5 activity. In other embodiments, the claimed method further comprises selecting a compound that inhibits TRPM5 activity.

In additional embodiments, the claimed method is directed to screening cells that are located in a multi-well vessel. The multi-well vessels of the claimed invention may contain up to and a number equaling 96 wells. In another embodiment, the multi-well vessel comprises greater than 96 wells. In another embodiment, the multi-well vessel comprises 384 wells. In yet another embodiment, the multi-well vessel comprises 1536 wells.

In some embodiments of the claimed invention, agents that increase calcium concentration are selected from the group consisting of: thrombin, adenosine triphosphate (ATP), carbachol, and agonists of endogenous G protein coupled receptors (GPCRs). In one embodiment of the invention, the agent that increases calcium concentration is a calcium ionophore, e.g. A23187, calcimycin or ionomycin.

In some embodiments of the claimed invention, the membrane potential fluorescent dye is a FMP dye.

In additional embodiments of the claimed invention, the optical detector is selected from the group consisting of: Fluorescent Imaging Plate Reader (FLIPR®, FLEXStation, Voltage/Ion Probe Reader (VIPR), fluorescent microscope and charge-coupled device (CCD) camera, and Pathway HT. In one embodiment of the invention, the optical detector is a FLIPR®.

Further embodiments, features, and advantages of the present inventions, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate one or more embodiments of the present invention and, together with the description, further serve to explain the principles of the invention and to enable a person skilled in the pertinent art to make and use the invention.

FIG. 1 shows a demonstration of TRPM5-dependent fluorescent signaling in Chinese Hamster Ovary (CHO) cells. CHO cells transfected with both the human TRPM5 ion channel and with the muscarinic 1 (M1) G protein coupled receptor (GPCR) were loaded with membrane potential dye and stimulated with carbachol, an M1 agonist. This GPCR activation triggers an increase in intracellular calcium ions in the cell, which in turn opens the TRPM5 ion channel letting primarily sodium ions into the cell. This depolarization increases the fluorescent signal of the dye which is measured on the Fluorescent Imaging Plate Reader (FLIPR®). Note that in an assay analyzing the effect of compounds on TRPM5, the compound would be added prior to activation of TRPM5.

FIGS. 3A-C show TRPM5 responses in transfected cells in response to three GPCR agonists: thrombin (FIG. 3A), carbachol (FIG. 3B) and adenosine triphosphate (ATP) (FIG. 3C) measured using a FLEXstation.

Figure 4:
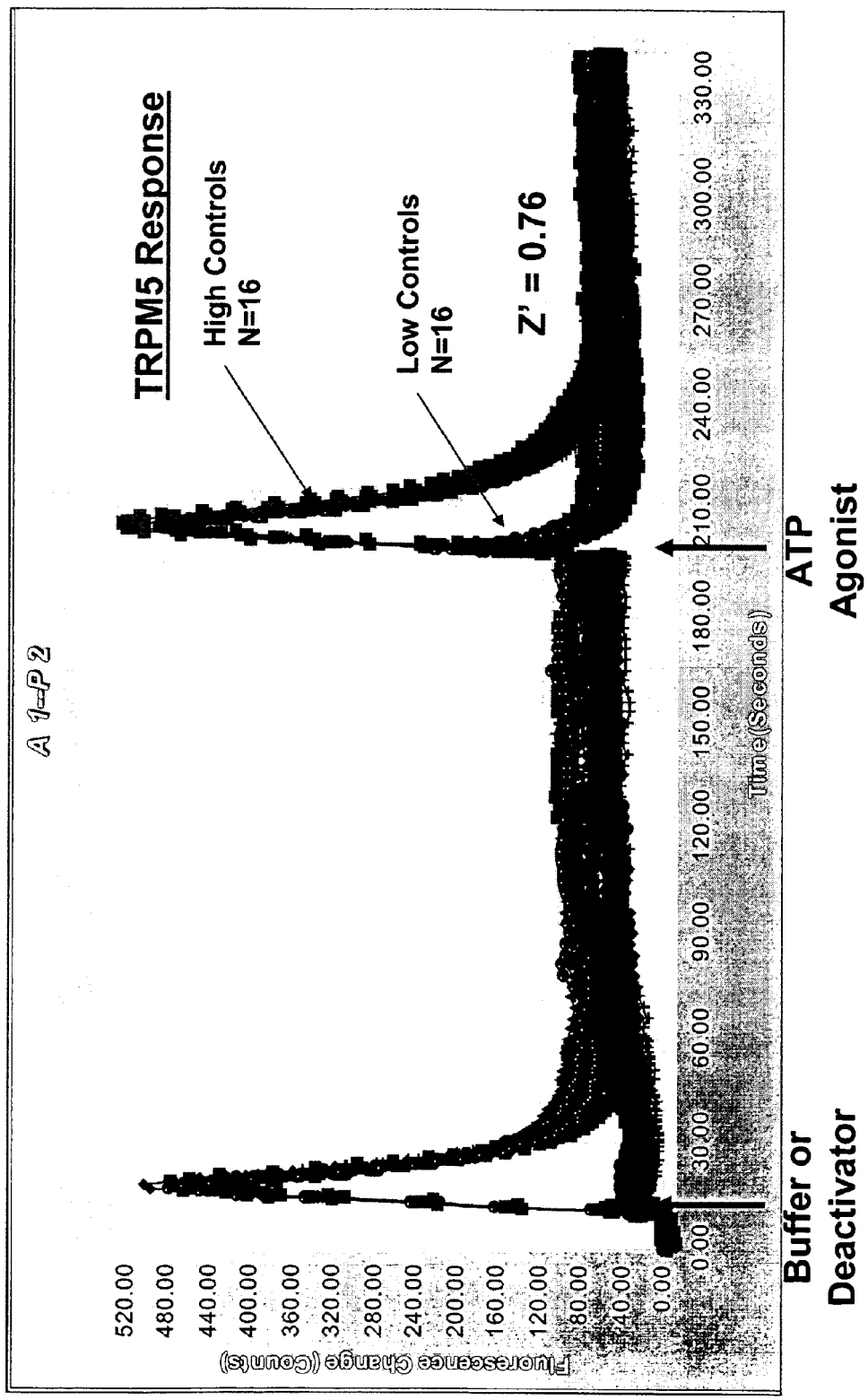

FIG. 4 shows High and Low controls for the TRPM5 high throughput screening assay using a FLIPR-Tetra™. The assay has a high signal to noise (High Control vs Low Controls) with a Z' value of 0.76. A value of Z'>0.5 indicates a robust assay for high throughput screening. (Zhang, J. H. et al. *J. Biomol. Screen.* 4:67-73 (1999)). (Z'=1−((3*$SD_{HC}$+ 3*$SD_{LC}$)/($AVG_{HC}$−$AVG_{LC}$)).

FIGS. 5A-5C show stimulation of cells stably expressing TRPM5 using ATP (FIG. 5A), carbachol (FIG. 5B) or thrombin (FIG. 5C) measured using a FLIPR®.

FIG. 6 shows results from a TRPM5 high throughput screen on greater than 85,000 compounds. The data is presented as frequency distribution of percent inhibition of control responses. Each compound was tested at a concentration of 10 µM.

FIG. 7 shows a schematic representation of the TRPM5 specificity filter using Ca++ response and KCl counterscreen assays.

FIGS. 8A-8B show that KCl counterscreen (FIG. 8A) and Ca++ flux (FIG. 8B) filters identify non-selective inhibitory compounds.

Figure 9A:
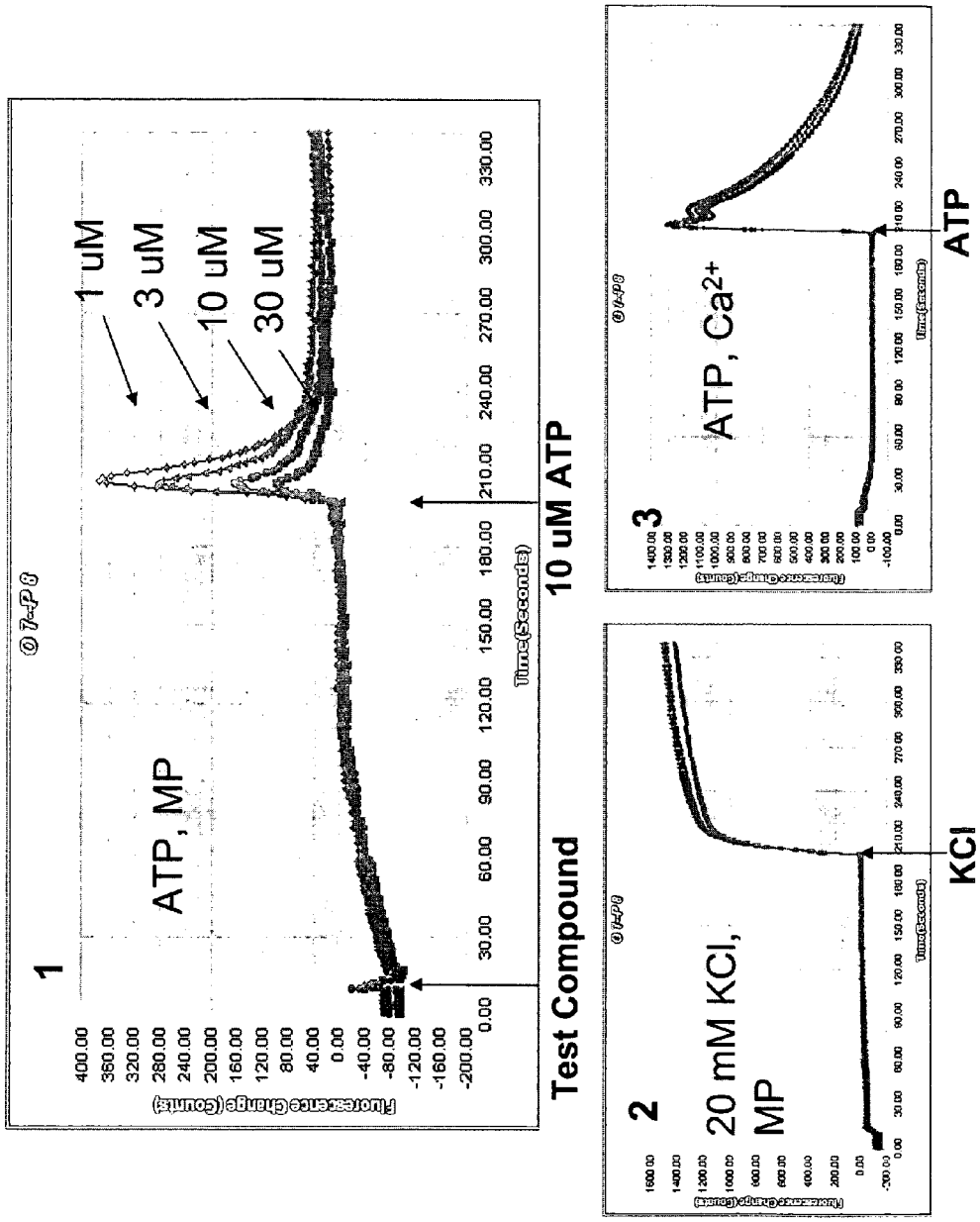
Figure 9B:
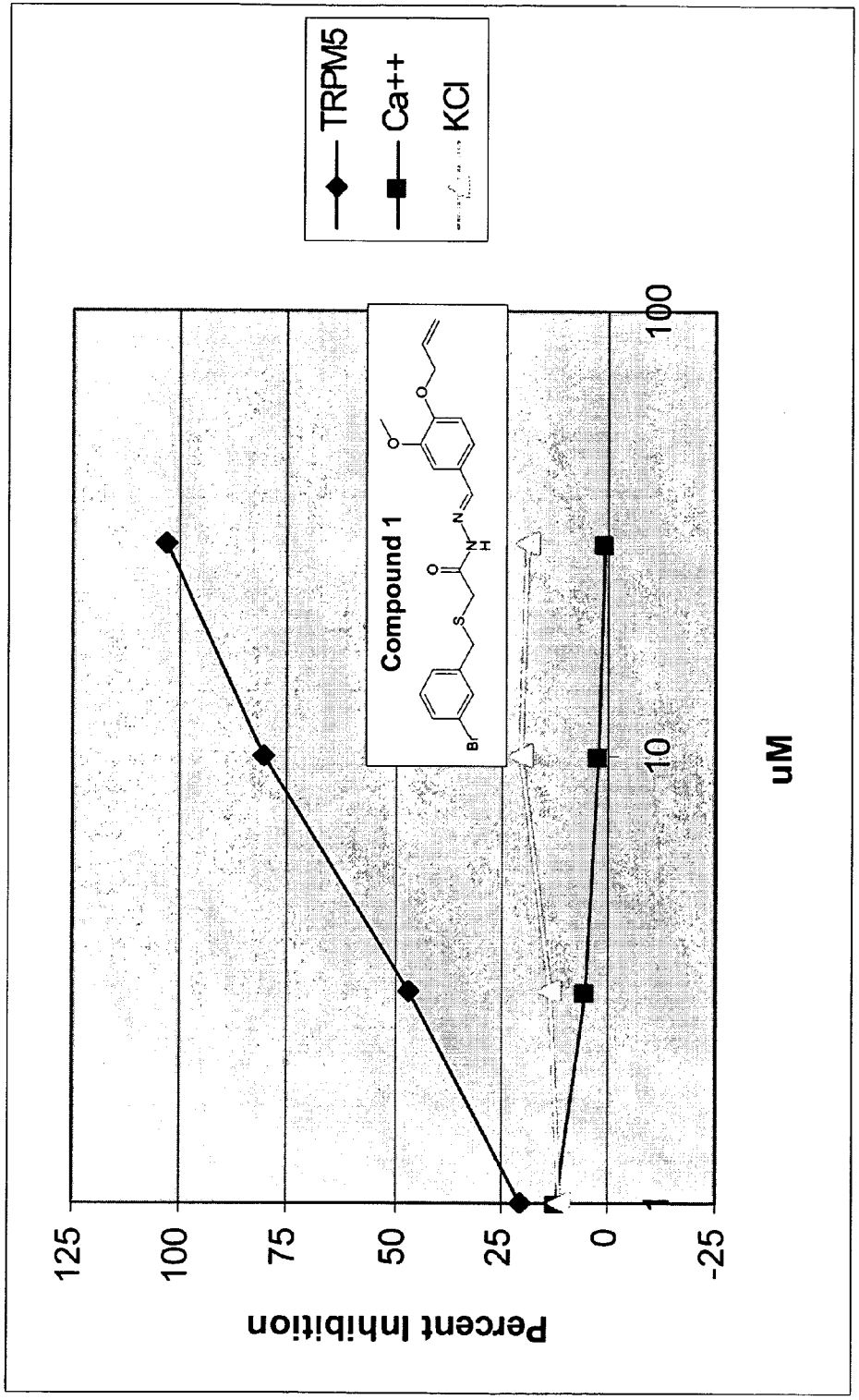

FIGS. 9A-9C show the usefulness of the KCl counterscreen in the TRPM5 assay to identify TRPM5-specific inhibitors. FIG. 9A demonstrates the identification of a TRPM5-specific inhibitor measured using a FLIPR®. FIG. 9B shows a dose responsive inhibition of TRPM5 by a compound without inhibiting KCl depolarization or inhibition of calcium flux activation. FIG. 9C shows two examples of non-specific inhibition of TRPM5.

Figure 10:
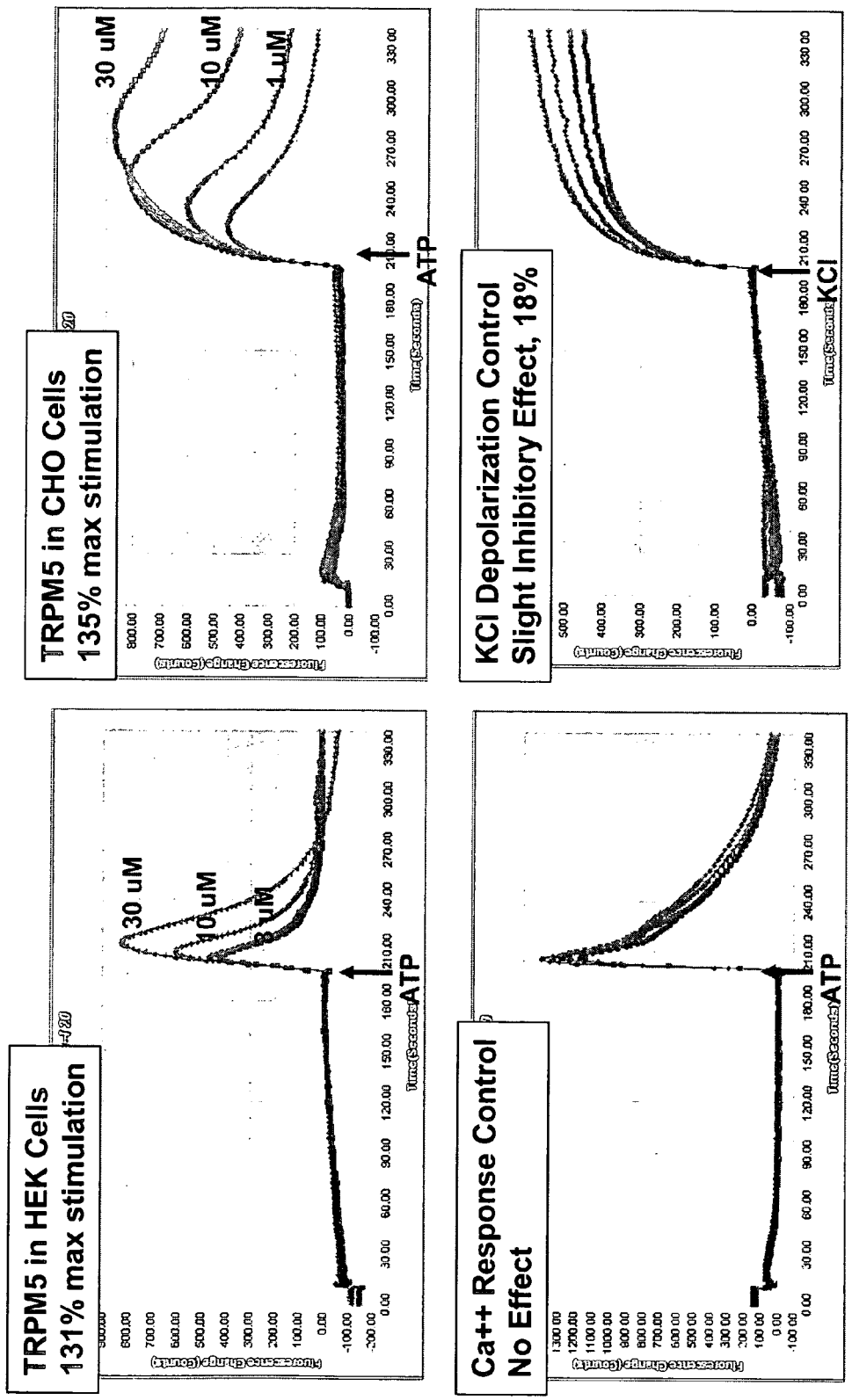

FIG. 10 shows the ability of the KCl counterscreen in the TRPM5 assay to identify TRPM5-specific enhancer compounds.

Figure 11:
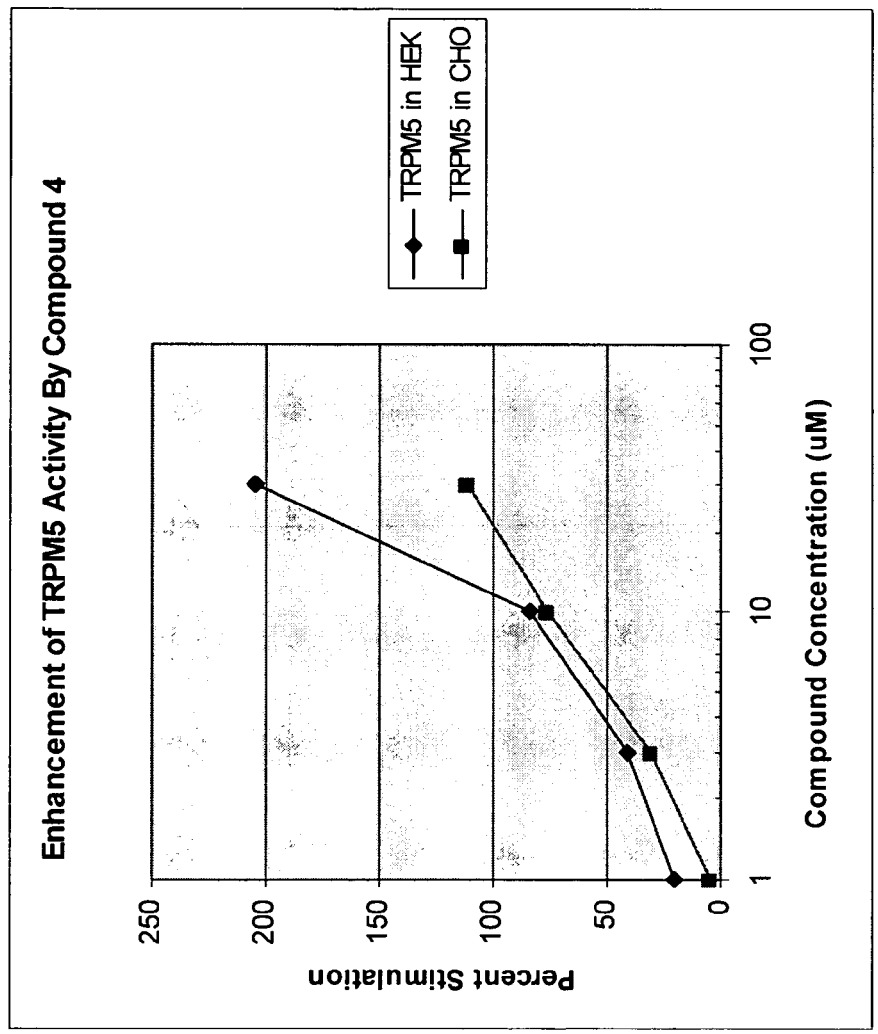

FIG. 11 shows the dose responsive stimulation of TRPM5 activity using a TRPM5-specific enhancer (compound 4).

Figure 12:
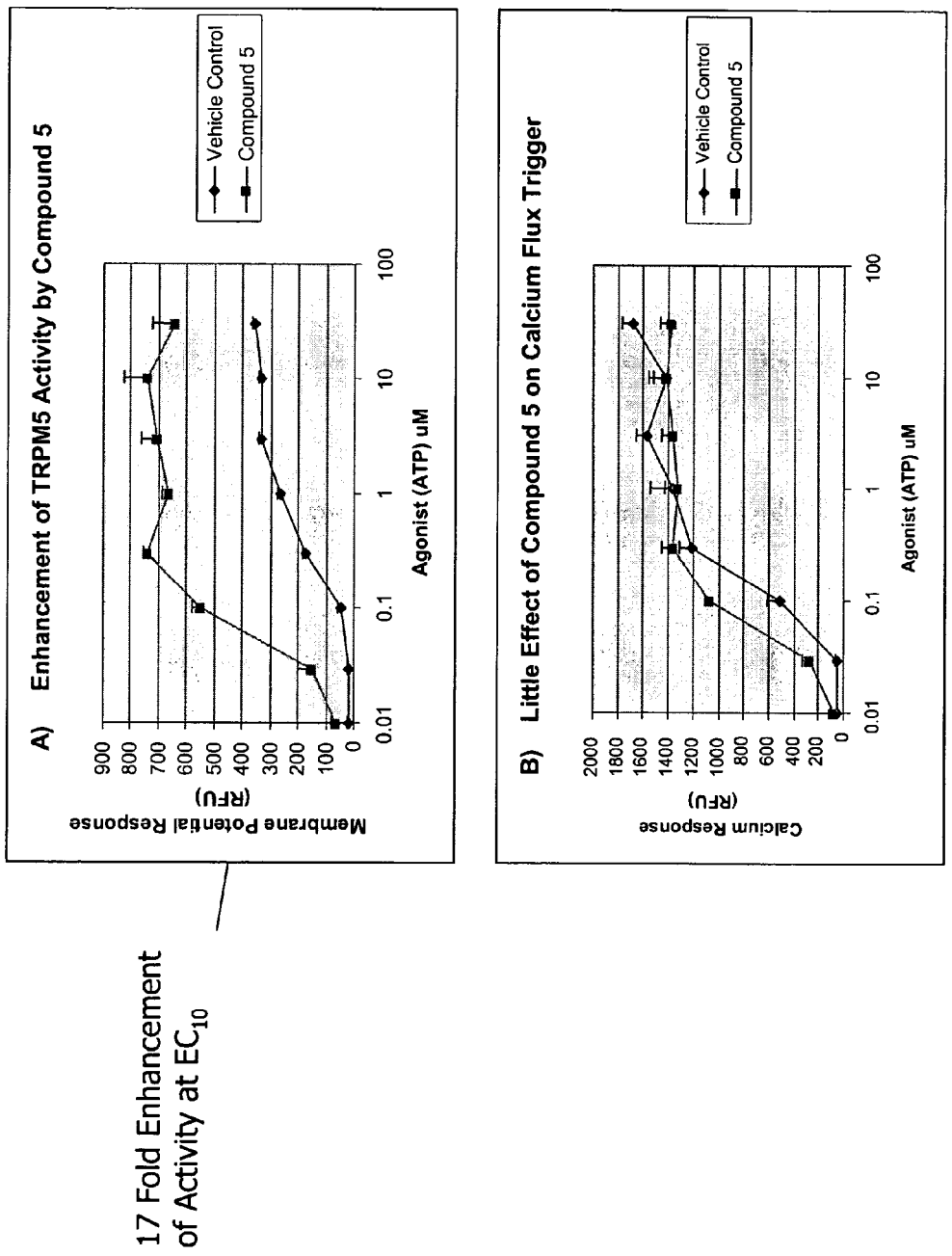

FIG. 12 shows that compound 5 (30 µM) produces a very strong enhancement (17 fold at $EC_{10}$) of TRPM5 particularly at suboptimal concentrations of ATP.

Figure 13A:
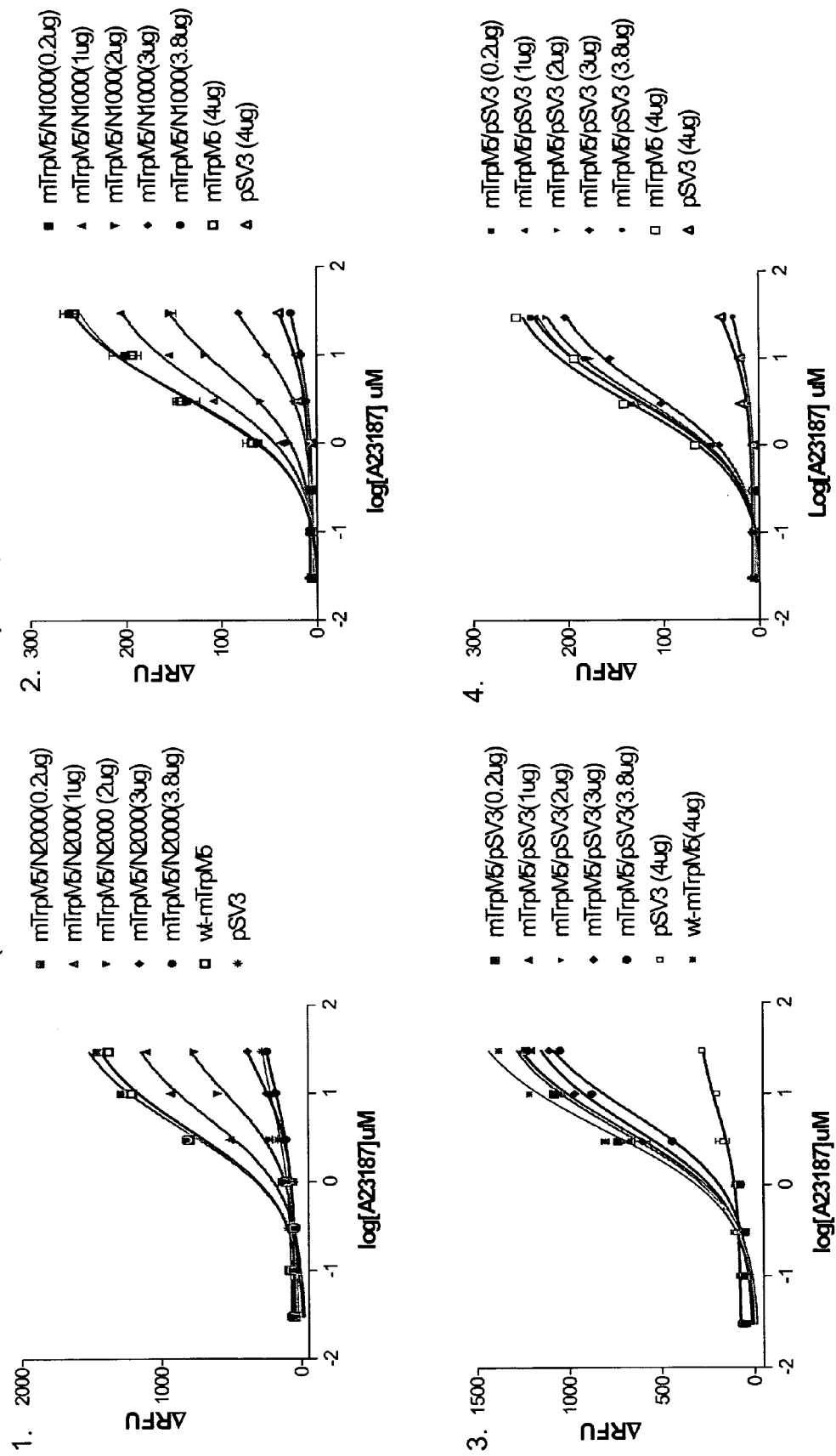
Figure 13B:
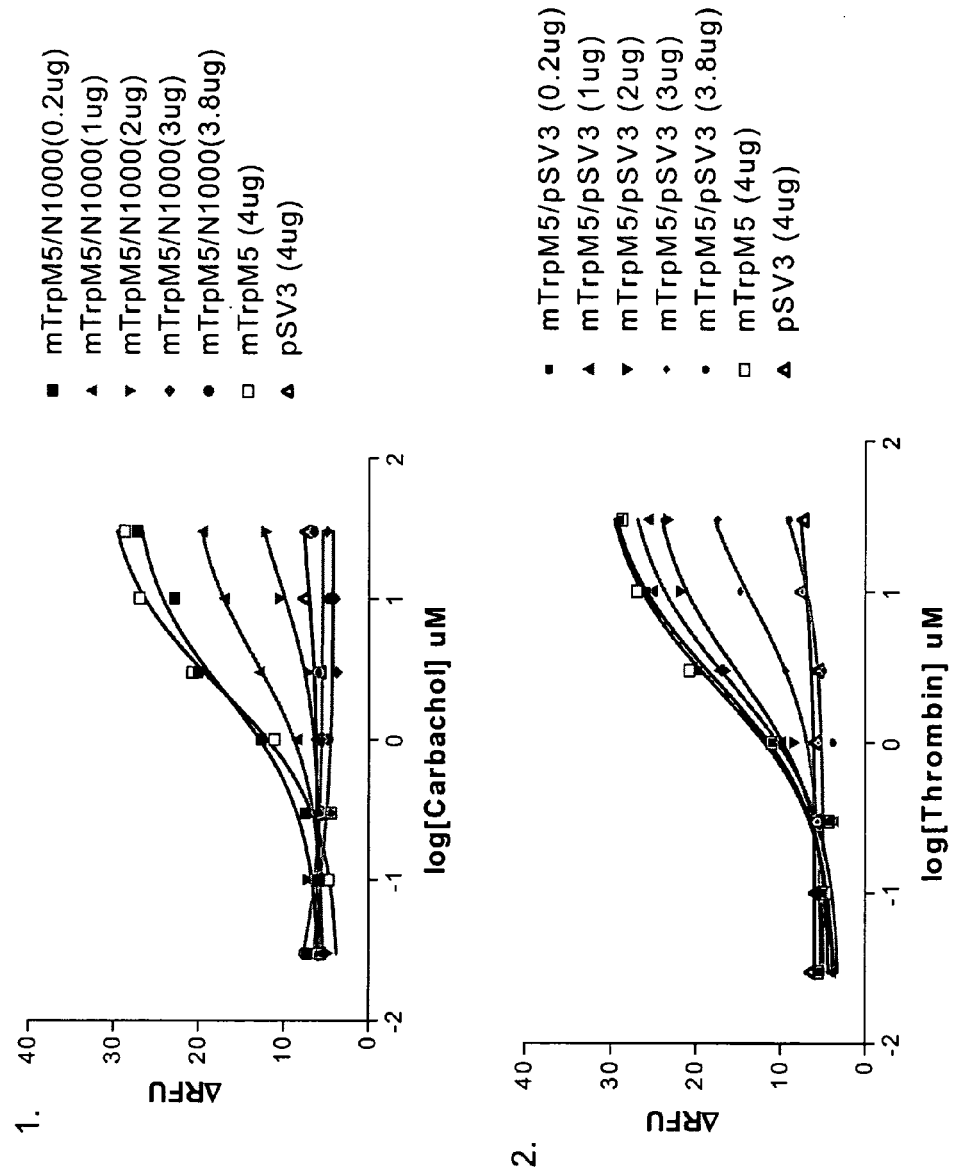

FIGS. 13A-13B shows the effect of a TRPM5 deletion mutant on the ability of the calcium ionophore A23187 (FIG. 13A) or carbachol (FIG. 13B) to cause TRPM5-mediated stimulation.

DETAILED DESCRIPTION OF THE INVENTION

Overview

The invention is a high throughput screening assay for compounds that modulate the activity of TRPM5. Since regulators of TRPM5 are likely to affect taste sensation, the invention, therefore, provides the first high throughput screening method useful for the identification of tastants that may specifically modulate TRPM5. This method is more selective than other screens for compounds that may impact taste because this method employs counterscreening, the use of suboptimal dosing, and dominant negative mutants of TRPM5.

High throughput refers to processing many compounds in a short time period. For example, using the invention, greater than 1000 test compounds may be screened for the ability to modulate TRPM5 activity in one hour. This assay is performed using a cell that expresses TRPM5. As used in the specification and claims, the singular form "a", "an" and "the" include plural references unless the context clearly dictates otherwise. For example, the term "an ion channel" includes a plurality of ion channels. The term "a cell" includes a plurality of cells.

The cell is exposed to a test compound and the ability of that compound to stimulate opening or to block opening of the channel is measured. The effect of the test compound is determined by measuring the change in the cell membrane potential after the cell is exposed to the compound. A fluorescent dye that responds to changes in cell membrane potential is used for detection. A means of evaluating specificity of the ability of the compound to modulate the channel is performed in parallel with the above described method. These parallel methods include the use of a potassium chloride counterscreen, the use of suboptimal doses of compounds known to stimulate the channel, and the use of a dominant-negative TRPM5 channel that is biologically inactive.

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

Cells

Cells for use in the method of the invention contain either a functional or non-functional TRPM5. The practitioner may use cells in which TRPM5 is endogenous or may introduce TRPM5 into a cell. If TRPM5 is endogenous to the cell, but the level of expression is not optimum, the practitioner may increase the level of expression of TRPM5 in the cell. Where a given cell does not produce TRPM5 at all, or at sufficient levels, a TRPM5 nucleic acid may be introduced into a host cell for expression and insertion into the cell membrane. The introduction, which may be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. General aspects of mammalian cell host system transformations have been described in U.S. Pat. No. 4,399,216. For various techniques for transforming mammalian cells, see Keown et al., Meth. Enzym., 185:527-537 (1990) and Mansour et al., Nature 336:348-352 (1988). As is described in detail below, TRPM5 can also be rendered non-functional. Biologically inactive TRPM5 can be introduced into cells using any of the above-described techniques. Cells expressing inactive TRPM5 are useful for confirmation of the specificity of TRPM5 activation.

The TRPM5 gene is expressed as a 4.5 kb transcript in a variety of fetal and adult tissues (Prawitt et al. Hum. Mol. Gen. 9:203-216 (2000)). Human TRPM5 has a putative reading frame containing 24 exons which encode an 1165 amino acid, membrane spanning polypeptide. The National Center for Biotechnology Information (NCBI) database lists several sequences for both the nucleic acid (NP_064673, NP_055370, AAP44477, AAP44476) and amino acid (NM_014555, NM_020277, AY280364, AY280365) sequences for both the human and mouse forms of TRPM5, respectively. The inclusion of the above sequences is for the purpose of illustration of the TRPM5 genetic sequence, however the invention is not limited to one of the disclosed sequences.

It is recognized in the art that there can be significant heterogeneity in a gene sequence depending on the source of the isolated sequence. The invention contemplates the use of conservatively modified variants of TRPM5. Conservatively modified variants applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W. H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

Dominant negative forms of TRPM5 may also be used in the high throughput screening assay to identify compounds that specifically modulate TRPM5. By "dominant negative" herein is meant a protein comprising at least one variant TRPM5 monomer that competes for binding to wildtype subunits such that the protein retains the ability to form an ion channel but it cannot regulate the flux of monovalent cations. Depending on the composition of the ion channel, the degree to which monovalent cation flux is inhibited will vary.

The variant TRPM5 proteins of the invention comprise non-conservative modifications (e.g. substitutions). By "non-conservative" modification herein is meant a modification in which the wildtype residue and the mutant residue differ significantly in one or more physical properties, including hydrophobicity, charge, size, and shape. For example, modifications from a polar residue to a nonpolar residue or vice-versa, modifications from positively charged residues to negatively charged residues or vice versa, and modifications from large residues to small residues or vice versa are non-conservative modifications. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. In one embodiment, the variant TRPM5 proteins of the present invention have at least one nonconservative modification. In one embodiment, the variant TRPM5 protein results from translation of a polynucleotide in which the first 1000 base pairs of the TRPM5 gene have been deleted. In another embodiment, the variant TRPM5 protein results from translation of a polynucleotide in which the first 2000 base pairs of the TRPM5 gene have been deleted.

The variant proteins may be generated, for example, by using a PDA™ system previously described in U.S. Pat. Nos. 6,188,965; 6,296,312; 6,403,312; alanine scanning (see U.S. Pat. No. 5,506,107), gene shuffling (WO 01/25277), site saturation mutagenesis, mean field, sequence homology, polymerase chain reaction (PCR) or other methods known to those of skill in the art that guide the selection of point or deletion mutation sites and types.

The cells used in methods of the present invention may be present in, or extracted from, organisms, may be cells or cell lines transiently or permanently transfected or transformed with the appropriate proteins or nucleic acids encoding them, or may be cells or cell lines that express the required TRPM5 from endogenous (i.e. not artificially introduced) genes.

Expression of the TRPM5 protein refers to the translation of the TRPM5 polypeptide from a TRPM5 gene sequence either from an endogenous gene or from nucleic acid introduced into a cell. The term "in situ" where used herein includes all these possibilities. Thus in situ methods may be performed in a suitably responsive cell line which expresses the TRPM5 (either as a native channel, or from a nucleic acid introduced into the cell). The cell line may be in tissue culture or may be, for example, a cell line xenograft in a non-human animal subject.

As used herein, the term "cell membrane" refers to a lipid bilayer surrounding a biological compartment, and encompasses an entire cell comprising such a membrane, or a portion of a cell.

For stable transfection of mammalian cells, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cell along with the gene of interest. Preferred selectable markers include those which confer resistance to drugs, such as G418, hygromycin and methotrexate. A nucleic acid encoding a selectable marker can be introduced into a host cell in the same vector as that encoding TRPM5, or can be introduced in a separate vector. Cells stably transfected with the introduced nucleic acid can be identified by drug selection (e.g., cells that have incorporated the selectable marker gene will survive, while the other cells die).

It should be noted that expression of TRPM5 can also be controlled by any of a number of inducible promoters known in the art, such as a tetracycline responsive element, TRE. For example, TRPM5 can be selectively presented on the cell membrane by controlled expression using the Tet-on and Tet-off expression systems provided by Clontech (Gossen, M. and Bujard, H. *Proc. Natl. Acad. Sci. USA* 89: 5547-5551 (1992)). In the Tet-on system, gene expression is activated by the addition of a tetracycline derivative doxycycline (Dox), whereas in the Tet-off system, gene expression is turned on by the withdrawal of tetracyline (Tc) or Dox. Any other inducible mammalian gene expression system may also be used. Examples include systems using heat shock factors, steroid hormones, heavy metal ions, phorbol ester and interferons to conditionally expressing genes in mammalian cells.

The cell lines used in assays of the invention may be used to achieve transient expression of TRPM5, or may be stably transfected with constructs that express a TRPM5 peptide. Means to generate stably transformed cell lines are well known in the art and such means may be used here. Examples of cells include, but are not limited to Chinese Hamster Ovary (CHO) cells, COS-7, HeLa, HEK 293, PC-12, and BAF.

The level of TRPM5 expression in a cell may be increased by introducing a TRPM5 nucleic acid into the cells or by causing or allowing expression from a heterologous nucleic acid encoding TRPM5. A cell may be used that endogenously expresses TRPM5 without the introduction of heterologous genes. Such a cell may endogenously express sufficient levels of TRPM5 for use in the methods of the invention, or may express only low levels of TRPM5 which require supplementation as described herein.

The level of TRPM5 expression in a cell may also be increased by increasing the levels of expression of the endogenous gene. Endogenous gene activation techniques are known in the art and include, but are not limited to, the use of viral promoters (WO 93/09222; WO 94/12650 and WO 95/31560) and artificial transcription factors (Park et al. *Nat. Biotech.* 21:1208-1214 (2003).

The level of TRPM5 expression in a cell may be determined by techniques known in the art, including but not limited to, nucleic acid hybridization, polymerase chain reaction, RNase protection, dot blotting, immunocytochemistry and Western blotting. Alternatively, TRPM5 expression can be measured using a reporter gene system. Such systems, which include for example red or green fluorescent protein (see, e.g. Mistili and Spector, *Nature Biotechnology* 15:961-964 (1997), allow visualization of the reporter gene using standard techniques known to those of skill in the art, for example, fluorescence microscopy. Furthermore, the ability of TRPM5 to be activated by known positive modulating compounds, such as thrombin, may be determined following manipulation of the TRPM5 expressing cells.

Cells described herein may be cultured in any conventional nutrient media. The culture conditions, such as media, temperature, pH and the like, can be selected by the skilled artisan without undue experimentation. In general, principles, protocols, and practical techniques for maximizing the productivity of cell cultures can be found in "Mammalian Cell Biotechnology: a Practical Approach", M. Butler, ed. JRL Press, (1991) and Sambrook et al, supra.

Intracellular Calcium Activation

TRPM5 is a calcium-activated ion channel permeable to monovalent cations such as sodium. Therefore, in order to observe channel activity, calcium stores within the cells must first be activated. There are many methods to activate intracellular calcium stores and many calcium activating agents are known in the art and include, but are not limited to thrombin, adenosine triphosphate (ATP), carbachol, and calcium ionophores (e.g. A23187). While nanomolar increases in calcium concentration ranges are required for TRPM5 channel activation, the concentration ranges useful for the claimed invention are known in the art, e.g., between $10^{-10}$ to $10^{-4}$ M for ATP, however, the precise concentration may vary depending on a variety of factors including cell type and time of incubation. The increased calcium concentration can be confirmed using calcium sensitive dyes, e.g., Fluo 3, Fluo 4, or FLIPR calcium 3 dye and single cell imaging techniques in conjunction with Fura2.

As described below, application of suboptimal doses of calcium activating agents can be used as a secondary screen for TRPM5 modulating specificity. Test cells are incubated with lower doses of the calcium activating agents described above, such that a fluorescent response that is lower than the maximum achievable response is generated. Generally, the dose is referred to as the effect concentration or $EC_{20-30}$, which relates to the effect condition where the fluorescent intensity is 20-30% of the maximal response. As used herein, "EC" refers to effect condition, such that $EC_{20}$ refers to the effect condition where the fluorescent intensity is 20% of the maximal response is generated. Upon the addition of a TRPM5-specific activating compound, this low response will be increased to at, or near, maximal levels of activation.

Counterscreening techniques are also useful for identifying TRPM5-specific modulating compounds. The ability to distinguish compounds specific for TRPM5 inhibition and activation from compounds that modulate other ion channels, in addition to, or instead of TRPM5, particularly channels not involved in taste transduction is vital. As described in greater detail below, potassium chloride non-specifically activates a number of ion channels, but not TRPM5. Therefore, KCl activation can be used as a counterscreen to identify TRPM5-specific modulating compounds.

Fluorescent Dyes

Voltage sensitive dyes that may be used in the assays and methods of the invention have been used to address cellular membrane potentials (Zochowski et al., *Biol. Bull.* 198:1-21 (2000)). Membrane potential dyes or voltage-sensitive dyes refer to molecules or combinations of molecules that enter depolarized cells, bind to intracellular proteins or membranes and exhibit enhanced fluorescence. These dyes can be used to detect changes in the activity of an ion channel such as TRPM5, expressed in a cell. Voltage-sensitive dyes include, but are not limited to, modified bisoxonol dyes, sodium dyes, potassium dyes and thorium dyes. The dyes enter cells and bind to intracellular proteins or membranes, therein exhibiting enhanced fluorescence and red spectral shifts (Epps et al., *Chem. Phys. Lipids* 69:137-150 (1994)). Increased depolarization results in more influx of the anionic dye and thus an increase in fluorescence.

The TRPM5 cells of the assay are preloaded with the membrane potential dyes for 30-240 minutes prior to addition of test compounds. Preloading refers to the addition of the fluorescent dye for a period prior to test compound addition during which the dye enters the cell and binds to intracellular lipophilic moieties.

In one embodiment, the membrane potential dyes are FMP dyes available from Molecular Devices (Catalog Nos. R8034, R8123). In other embodiments, suitable dyes could include dual wavelength FRET-based dyes such as DiSBAC2, DiSBAC3, and CC-2-DMPE (Invitrogen Cat. No. K1016). [Chemical Name Pacific Blue™ 1,2-ditetradecanoyl-sn-glycero-3-phosphoethanolamine, triethylammonium salt]. Cells are typically treated with 1 to 10 µM buffered solutions of the dye for 20 to 60 minutes at 37° C.

Dyes that measure intracellular calcium levels are also used to confirm TRPM5 specificity. In one embodiment, the intracellular calcium dye is the FLIPR Calcium 3 dye available from Molecular Devices (Part Number: R8091). In other embodiments, suitable dyes such as Fluo-3, Fluo-4 (Invitrogen (Cat. Numbers F14242 and F14202) can be used to measure increases in intercellular calcium. Cells are typically treated with 1 to 10 µM buffered solutions of the dye for 20 to 60 minutes at 37° C. In some cases it is necessary to remove the dye solutions from the cells and add fresh assay buffer before proceeding with the assay.

Assay Detection

Detecting and recording alterations in the spectral characteristics of the dye in response to changes in membrane potential may be performed by any means known to those skilled in the art. As used herein, a "recording" refers to collecting and/or storing data obtained from processed fluorescent signals, such as are obtained in fluorescent imaging analysis.

In some embodiments, the assays of the present invention are performed on isolated cells using microscopic imaging to detect changes in spectral (i.e., fluorescent) properties. In other embodiments, the assay is performed in a multi-well format and spectral characteristics are determined using a microplate reader.

By "well" it is meant generally a bounded area within a container, which may be either discrete (e.g., to provide for an isolated sample) or in communication with one or more other bounded areas (e.g., to provide for fluid communication between one or more samples in a well). For example, cells grown on a substrate are normally contained within a well that may also contain culture medium for living cells. Substrates can comprise any suitable material, such as plastic, glass, and the like. Plastic is conventionally used for maintenance and/or growth of cells in vitro.

A "multi-well vessel", as noted above, is an example of a substrate comprising more than one well in an array. Multi-well vessels useful in the invention can be of any of a variety of standard formats (e.g., plates having 2, 4, 6, 24, 96, 384, or 1536, etc., wells), but can also be in a non-standard format (e.g., plates having 3, 5, 7, etc., wells).

A suitable configuration for single cell imaging involves the use of a microscope equipped with a computer system. One example of such a configuration, ATTO's Attofluor® RatioVision® real-time digital fluorescence analyzer from Carl Zeiss, is a completely integrated work station for the analysis of fluorescent probes in living cells and prepared specimens (ATTO, Rockville, Md.). The system can observe ions either individually or simultaneously in combinations limited only by the optical properties of the probes in use. The standard imaging system is capable of performing multiple dye experiments such as FMP (for sodium) combined with GFP (for transfection) in the same cells over the same period of time. Ratio images and graphical data from multiple dyes are displayed online.

When the assays of the invention are performed in a multi-well format, a suitable device for detecting changes in spectral qualities of the dyes used is a multi-well microplate reader. Suitable devices are commercially available, for example, from Molecular Devices (FLEXstation® microplate reader and fluid transfer system or FLIPR® system), from Hamamatsu (FDSS 6000) and the "VIPR" voltage ion probe reader (Aurora, Bioscience Corp. CA, USA). The FLIPR-Tetra™ is a second generation reader that provides real-time kinetic cell-based assays using up to 1536 simultaneous liquid transfer systems. All of these systems can be used with commercially available dyes such as FMP, which excites in the visible wavelength range.

Using the FLIPR® system, the change in fluorescent intensity is monitored over time and is graphically displayed as shown, for example in FIGS. 9A-9C. The addition of TRPM5 enhancing compounds causes an increase in fluorescence, while TRPM5 blocking compounds block this increase.

Several commercial fluorescence detectors are available that can inject liquid into a single well or simultaneously into multiple wells. These include, but are not limited to, the Molecular Devices FlexStation (eight wells), BMG NovoStar (two wells) and Aurora VIPR (eight wells). Typically, these instruments require 12 to 96 minutes to read a 96-well plate in flash luminescence or fluorescence mode (1 min/well). An alternative method is to inject the modulator into all sample wells at the same time and measure the luminescence in the whole plate by imaging with a charge-coupled device (CCD) camera, similar to the way that calcium responses are read by calcium-sensitive fluorescent dyes in the FLIPR®, FLIPR-384 or FLIPR-Tetra™ instruments. Other fluorescence imaging systems with integrated liquid handling are expected from other commercial suppliers such as the second generation LEADSEEKER from Amersham, the Perkin Elmer Cell-Lux—Cellular Fluorescence Workstation and the Hamamatsu FDSS6000 System. These instruments can generally be configured to proper excitation and emission settings to read FMP dye ($540_{ex}\pm 15$ nm, $570_{em}\pm 15$ nm) and calcium dye ($490_{ex}\pm 15$ nm, $530_{em}\pm 15$ nm). The excitation/emission characteristics differ for each dye, therefore, the instruments are configured to detect the dye chosen for each assay.

Test Compounds

Test compounds employed in the screening methods of this invention include for example, without limitation, synthetic organic compounds, chemical compounds, naturally occurring products, polypeptides and peptides, nucleic acids, etc.

Essentially any chemical compound can be used as a potential modulator or ligand in the assays of the invention. Most often compounds dissolved in aqueous or organic (especially dimethyl sulfoxide- or DMSO-based) solutions are used. The assays are designed to screen large chemical libraries by automating the assay steps. The compounds are provided from any convenient source to the cells. The assays are typically run in parallel (e.g., in microtiter formats on microtiter plates in robotic assays with different test compounds in different wells on the same plate). It will be appreciated that there are many suppliers of chemical compounds, including ChemDiv (San Diego, Calif.), Sigma-Aldrich (St. Louis, Mo.), Fluka Chemika-Biochemica-Analytika (Buchs Switzerland) and the like.

"Modulating" as used herein includes any effect on the functional activity of TRPM5. This includes blocking or inhibiting the activity of the channel in the presence of, or in response to, an appropriate stimulator. Alternatively, modulators may enhance the activity of the channel. "Enhance" as used herein, includes any increase in the functional activity of TRPM5.

In one embodiment, the high throughput screening methods involve providing a small organic molecule or peptide library containing a large number of potential TRPM5 modulators. Such "chemical libraries" are then screened in one or more assays, as described herein, to identify those library members (particular chemical species or subclasses) that display a desired characteristic activity. The compounds thus identified can serve as conventional "lead compounds" or can themselves be used as potential or actual products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14:309-314 (1996) and PCTIUS96/10287), carbohydrate libraries (see, e.g., Liang et al., Science, 274:1520-1522 (1996) and U.S. Pat. No. 5,593,853), small organic molecule libraries (see, e.g., isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.; etc.).

Candidate agents, compounds, drugs, and the like encompass numerous chemical classes, though typically they are organic molecules, preferably small organic compounds having a molecular weight of more than 100 and less than about 10,000 daltons, preferably, less than about 2000 to 5000 daltons. Candidate compounds may comprise functional groups necessary for structural interaction with proteins, particularly hydrogen bonding, and typically include at least an amine, carbonyl, hydroxyl or carboxyl group, preferably at least two of the finctional chemical groups. The candidate compounds may comprise cyclical carbon or heterocyclic structures, and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof.

A variety of other reagents may be included in the screening assay according to the present invention. Such reagents include, but are not limited to, salts, solvents, neutral proteins, e.g. albumin, detergents, etc., which may be used to facilitate optimal protein-protein binding and/or to reduce non-specific or background interactions. Examples of solvents include, but are not limited to, dimethyl sulfoxide (DMSO), ethanol and acetone, and are generally used at a concentration of less than or equal to 1% (v/v) of the total assay volume. In addition, reagents that otherwise improve the efficiency of the assay, such as protease inhibitors, anti-microbial agents, etc. may be used. Further, the mixture of components in the method may be added in any order that provides for the requisite binding.

The compounds identified using the disclosed assay are potentially useful as ingredients or flavorants in ingestible compositions, i.e., foods and beverages as wells as orally administered medicinals. Compounds that modulate taste perception can be used alone or in combination as flavorants in foods or beverages. The amount of such compound(s) will be an amount that yields the desired degree of modulated taste perception of which starting concentrations may generally be between 0.1 and 1000 µM.

EXAMPLES

Example 1

Imaging-Based High Throughput Screening Assay Using Transiently-Transfected Cells As described in greater detail below, HEK 293 cells, transiently transfected with a plasmid bearing the human TRPM5 gene, were used to develop the high throughput screening assay. Indirect measurement of the changes in $Na^+$ ions within the HEK 293 cells were made using a FMP dye and stimulation of the cells using calcium activating agents.

Plasmid Construction

First strand cDNA was synthesized by Thermoscript RT-PCR System (Invitrogen) from human small intestine poly A+ RNA (BD Biosciences) and the full length hTRPM5 was amplified by PCR using GC Melt (BD Biosciences). The product was PCR purified by Pure Link PCR Purification (Invitrogen) and inserted into a vector using the TOPO TA Cloning Kit (Invitrogen). After sequencing, 6 mutations were found and the mutations were corrected using the Quick Change Multi Site Directed Mutagenesis Kit (Stratagene) in 2 rounds. Three mutations were corrected in each round. The full length TRPM5 was excised from the TOPO TA vector using the EcoRI and NotI restriction enzymes and ligated in the pENTR 3C vector, which had also been digested with EcoRI and NotI. The insert and vector bands were gel extracted and purified using the SNAP Gel Purification Kit (Invitrogen). Finally, LR Recombination Reaction (Invitrogen) was used to insert the entry clone into destination vectors of interest (e.g., pT-Rex-DEST 30, pcDNA-DEST 53, pcDNA 3.2/v5-DEST and pcDNA 6.2/V5-DEST).

Transfection $1.0 \times 10^6$ HEK 293 cells (ATCC) were plated in each well of a 6-well tissue culture dish overnight. The following day, cells were transfected with 4 µg of a pcDNA3.2 vector containing TRPM5 cDNA and 8 µl of Lipofectamine 2000 (Invitrogen), according to the manufacturer's protocol, and incubated overnight. The following day, transfected cells were trypsinized and seeded into 96-well black, clear bottom, poly-D-lysine plates (Corning) at a density of 70,000 cells/well in a 100 µl volume and incubated in a 37° C./5% $CO_2$ incubator overnight.

Fluorescence Microscopy

To confirm that the HEK transfected cells expressed TRPM5, cells transiently-transfected with 6 µg of plasmid DNA expressing TRPM5 (as described above) and grown on Lab TekII Chamber slides, were evaluated. Control, untransfected cells were grown in parallel with the transfected cells. The fluorescent emission of the GFP-TRPM5 expressing cells was detected using the green detection channel (515-530 nm) of a fluorescent microscope.

Membrane Potential Assay

Once the expression of TRPM5 was confirmed in the HEK cells, 100 µl of the Blue or Red FMP dye (Molecular Devices) was added to each well of plates seeded with the transiently transfected cells. The plate was then incubated in a 37° C./5% $CO_2$ incubator for 1 hour. The plate was read in a FLEXStation microplate reader (Molecular Devices) with an excitation of 530 nm and an emission of 565 nm. The fluorescence was monitored for 3 minutes upon exposure of the cells to a calcium activating agent (carbachol, thrombin peptide or ATP).

Results

Figure 1:
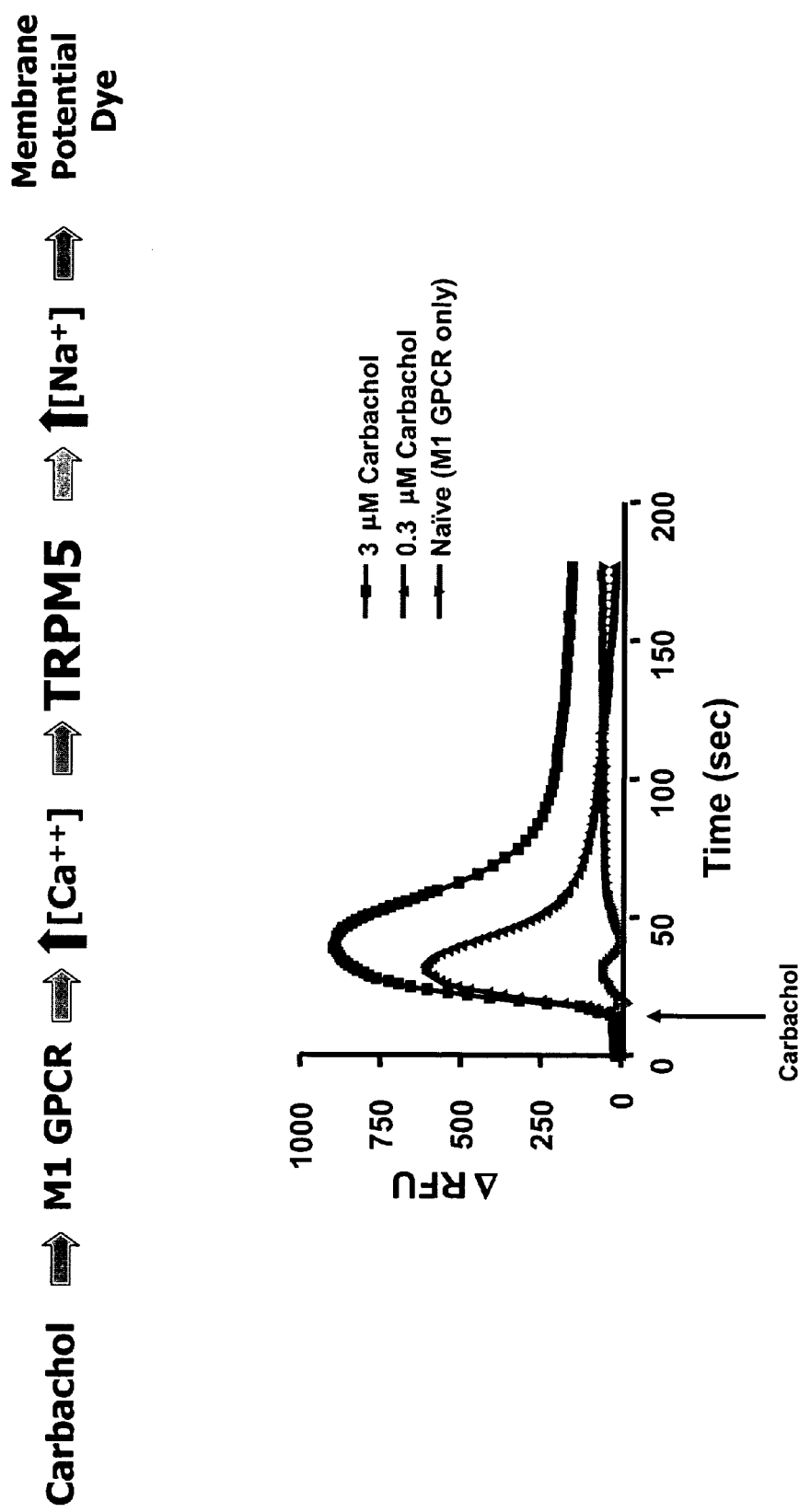
Figure 2:
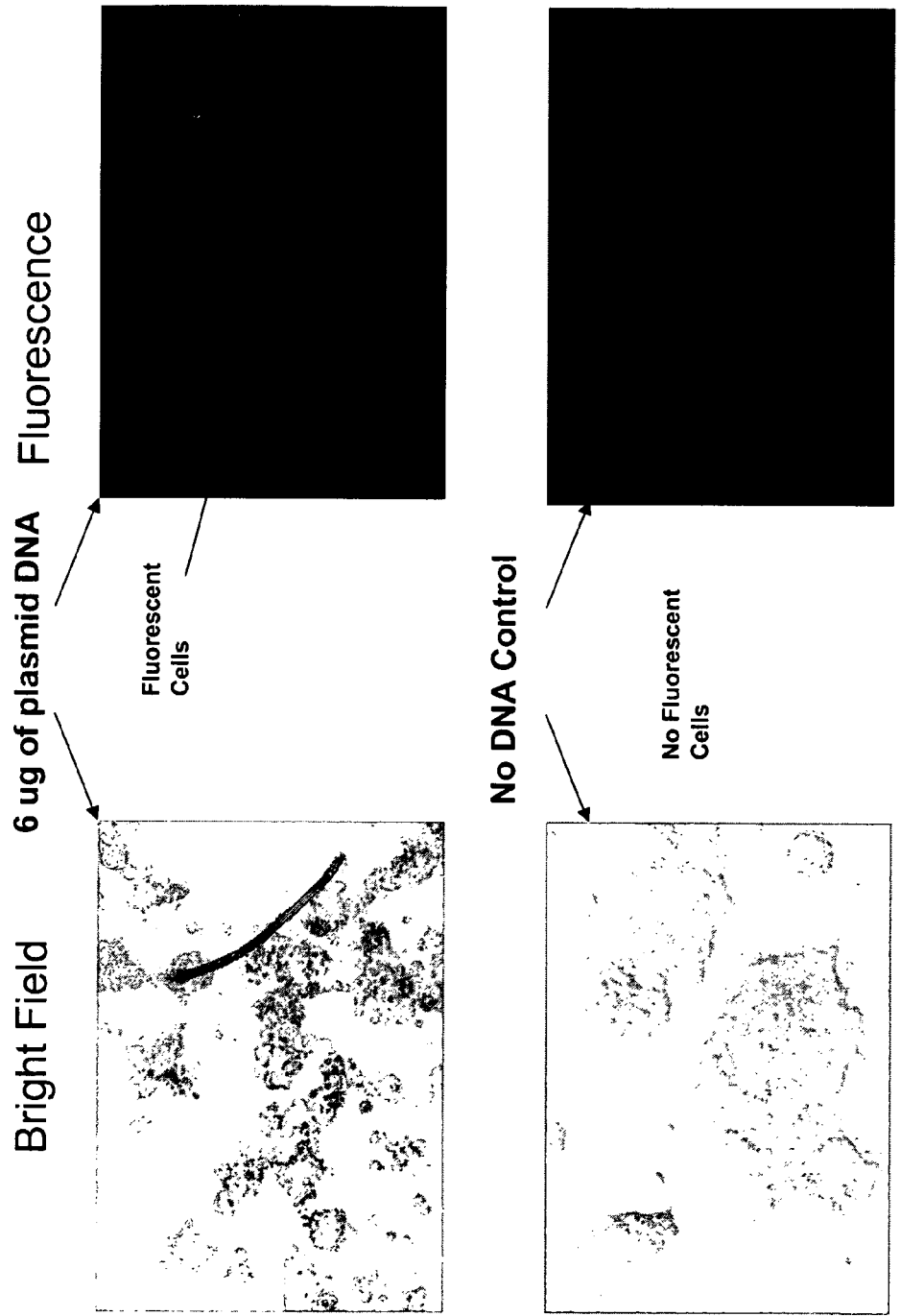
FIG. 2 shows TRPM5-GFP expression in transiently-transfected HEK 293 cells by fluorescence microscopy.

The TRPM5 plasmid was readily expressed as demonstrated by the appearance of bright green HEK 293 cells that were transfected with the GFP-TRPM5 plasmid (FIG. 2).

Figure 3:
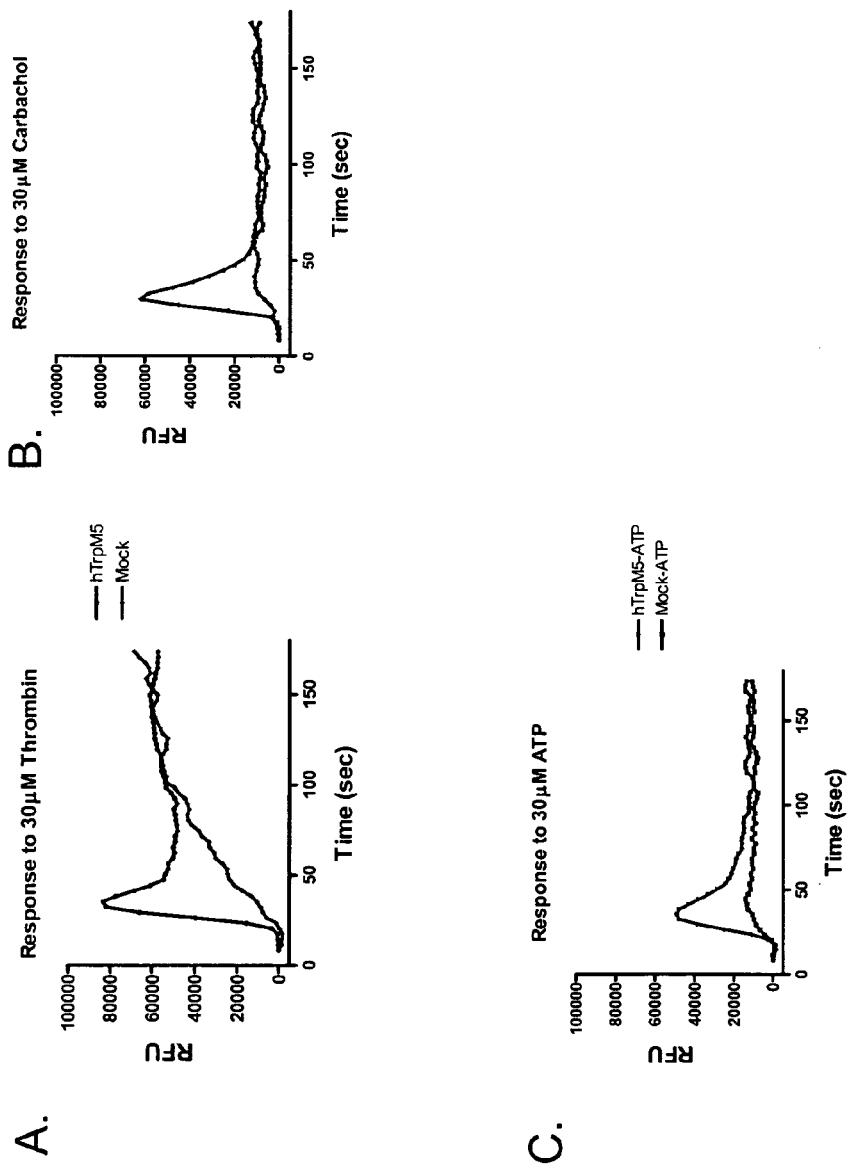
FIG. 3 shows TRPM5 ion channel responses in transiently transfected HEK 293 cells.

Demonstration of TRPM5 response to stimuli is shown in FIG. 3A-3C. TRPM5 transfected cells were loaded with FMP dye and then treated with thrombin (FIG. 3A), carbachol (FIG. 3B), or ATP (FIG. 3C) and monitored for an increase in cellular fluorescence in the FLEXstation. All three agents generated a strong spike in relative fluorescence within the first 30 seconds of agonist addition. The response was transient in nature as well, as fluorescence levels returned to near baseline levels by approximately 1 minute post-agonist addition. Mock treated cells produced a low response in both the ATP and carbachol treated cells, however a high degree of background fluorescence was observed in the thrombin treated group. The fluorescence of the thrombin treated cells was greater than 4-fold over background, therefore the background fluorescence did not interfere with data interpretation.

The applicability of the screening method of the invention to a high throughput format is demonstrated in FIG. 4, where samples in a 384-well plate were evaluated in a 5 minute assay on the FLIPR-Tetra™ (Molecular Devices). TRPM5-Transfected HEK cells, 15,000/well, were seeded overnight on poly-D-lysine coated 384 well plates in 20 µl media. Membrane potential dye, 20 µl/well, was added and the plates incubated for 1 hour at 37° C. Plates were placed in a FLIPR-Tetra™ and fluorescence readings were taken using appropriate filters. After 10 seconds, 10 µl of either buffer or a deactivating agent (ATP) were added to the cells (first addition). At 200 seconds a second addition of 10 µl of ATP was added to all cells. A strong, reproducible TRPM5 response was seen in those cells that received buffer (High Control), while those that were initially stimulated with ATP became deactivated and failed to respond to a second addition of ATP (Low Control). There was a >5 fold difference in peak heights (maximum-minimum values over each peak) between the High and Low controls, demonstrating that the assay is suitable for high throughput screening. Furthermore a calculation of Z'* gave a value of 0.76, greater than the HTS acceptable value of 0.5. ($Z'=1-((3*SD\text{high control}+3*SD \text{ low control})/(\text{High Control}-\text{Low Control}))$.

Example 2

Imaging-based High Throughput Screening Assay Using Stably-transfected Cells Stimulation of TRPM5 was also visible in HEK cells stably-expressing TRPM5. Following confirmation of TRPM5 expression, the ability to regulate TRPM5 activity was analyzed as described above.

Plasmid Construction and Transfection

HEK cells stably-expressing TRPM5 were generated using the pcDNA 3.2 vector containing hTRPM5 using the technique described above. Stable clones were generated by transfecting $1.0 \times 10^6$ HEK 293 cells with 4 µg of pcDNA 3.2-TrpM5 in a 35 mm tissue culture dish. Two days post-transfection, the cells were trypsinized and diluted 1:10 and 1:100 in growth medium containing 1 mg/ml Geneticin (Invitrogen) to select for single clones. Cells were maintained in this medium until single individual clones could be isolated and expanded. Upon selection of individual clones, cells were maintained in medium containing 0.25 mg/ml Geneticin to maintain the selective pressure. Individual clones were then examined with membrane potential dye in the FLEXstation or FLIPR® as described above. Those clones with the largest fluorescent response to ATP and carbachol were then selected and examined for further analysis. Selected clones with the highest $EC_{50}$ to ATP and carbachol were then expanded and used for the high throughput screening assays.

Results

Figure 5:
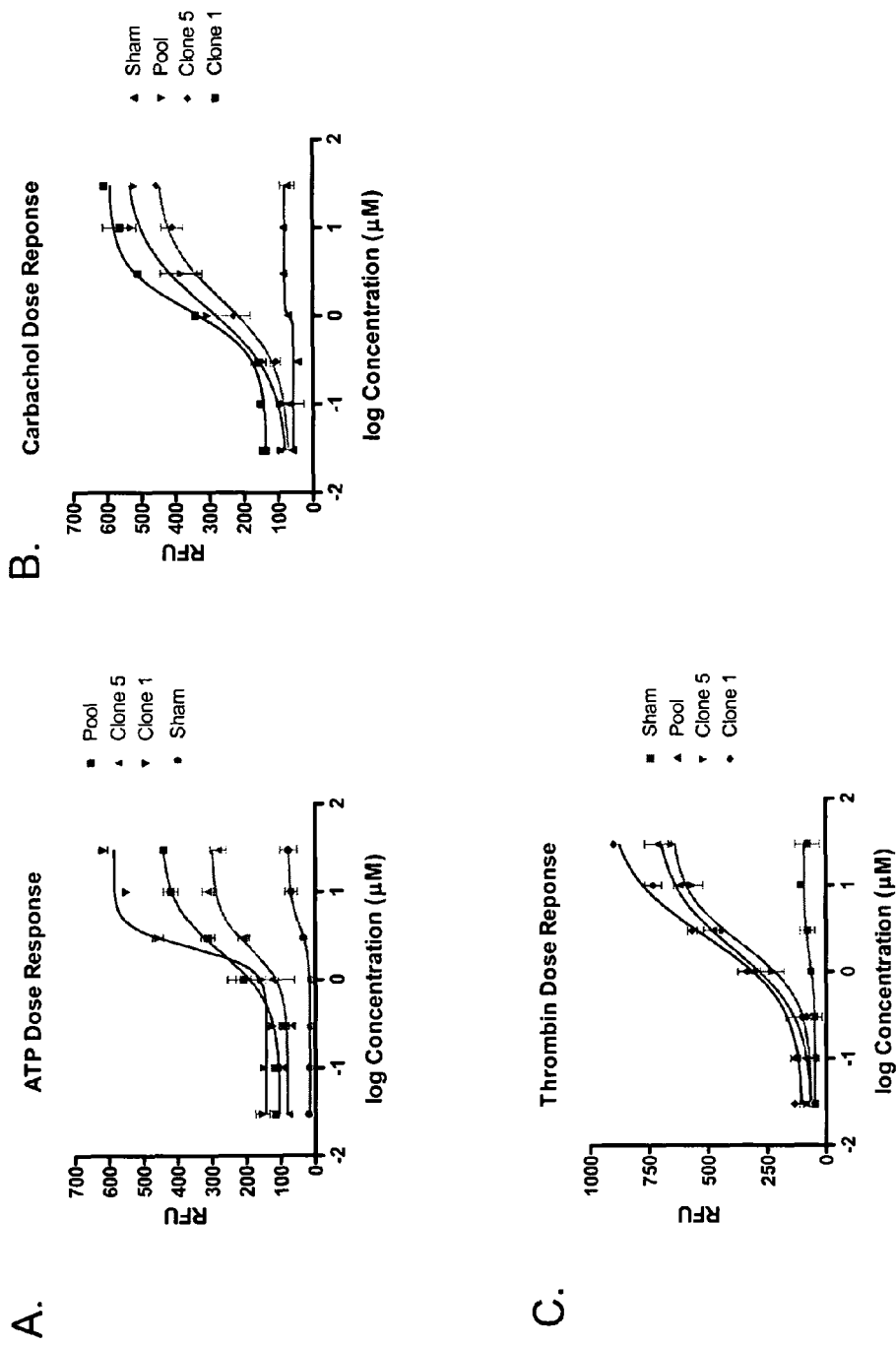

TRPM5 stably expressed in HEK cells was analyzed for its ability to respond to different concentrations of several GPCR agonists. The assay was performed on a FLIPR® using the excitation 510-545 nm and emission 565-625 nm filter sets. Assay plates containing stably expressing HEK cells were loaded with 1× Membrane Potential Assay Dye Red (Molecular Devices) for one hour in a 37° C. and 5% $CO_2$ incubator. The plates were then removed from the incubator and equilibrated to room temperature for 15 minutes before reading on the FLIPR®. The plates were read on the FLIPR® for a total of 3 minutes. Baseline fluorescence was obtained on the FLIPR® for 10 seconds followed by addition of each agonist by the FLIPR® and read for an additional 2 minutes and 50 seconds. FIG. 5 shows that two TRPM5-expressing clones were stimulated by varying concentrations of the GPCR agonists as evidenced by an increase in the relative fluorescence of TRPM5-expressing cells compared to sham transfected cells. The values on the graph represent the difference in the maximum minus the minimum fluorescence upon agonist addition. Individual clones are represented by clone number, while the pool of clones represents the sum of all cells that were resistant to selection. In all cases, clone 1 gave the strongest response to all 3 agonists (ATP, carbachol, and thrombin peptide, FIGS. 5A-5C, respectively). Clone 5 and pooled clones generated a lower response in comparison to clone 1. However, both the clone 5 and pool responses were a minimum 3-fold higher than fluorescence in non-transfected cells. Sham, non-transfected cells showed little or no response at any agonist concentration.

Example 3

High Throughput Screening Assay Using Suboptimal Concentrations of Calcium-activating Agents Specificity of potential activating compounds may be identified using suboptimal concentrations of agents that increase intracellular calcium levels. In this type of assay, rather than using a high concentration of, for example carbachol, a reduced concentration is added to TRPM5-expressing cells with or without an additional test compound. Enhancers of TRPM5 activity are those test compounds that increase the fluorescent intensity in reduced carbachol treated cells, to the level seen in cells treated to a high dose.

A carbachol dose response curve was generated for the TRPM5 expressing cells so that the suboptimal concentration range could be determined. Cells expressing TRPM5 were incubated with an $EC_{20}$-$EC_{30}$ level of carbachol (0.3 to 1 µM) prior to addition of test compounds. Mock incubated and $EC_{100}$ treated cells were used as controls. Test compounds that increased the fluorescent intensity of $EC_{20}$-$EC_{30}$ treated cells to levels approaching $EC_{100}$ treated cells were classified as activators of TRPM5.

Example 4

KCl Counterscreen for TRPM5 Specificity

The need for enhanced specificity assays for TRPM5 activation is shown in FIG. 6. Greater than 85,000 compounds were screened using the above-described high throughput screening assays and the Gaussian distribution of inhibition values was plotted. As is visible in the figure, most of the compounds were within the −25 to +25 percent range of inhibition of the control response. Therefore, in order to identify TRPM5 modulating compounds with greater specificity, compounds that also act on other ion channels would have to be removed from the analysis.

KCl activates a number of ion channels, but not TRPM5. Therefore, KCl can be used as a counterscreen to identify modulating compounds specific for TRPM5.

The ideal blocker would block TRPM5 but not other channels. The TRPM5 assay is conducted as described in Example 3, utilizing a membrane potential dye. A test compound is added, and the cells are then stimulated with ATP to trigger the channel, leading to a dye response. The process is shown schematically in FIG. 7. The KCl counterscreen is performed as described in Example 3, with identical cells, pretreated with the same compound, but the stimulus was 20 mM KCl, not ATP. KCl stimulated and unstimulated responses are used as controls. An example of a non-selective inhibitory compound as identified using the KCl counterscreen is shown in FIG. 8A. Compound F001344,A3 (structure shown below) inhibits TRPM5, but also the KCl responses (arrows). An additional specificity assay utilizes a Ca++ flux dye (Calcium 3 Dye, Part No. R8091) to determine whether or not the compound interferes with agonist-induced Ca++ flux response. An example of a non-selective inhibitory compound as identified by the Ca++ flux assay is shown in FIG. 8B. Compound F0013488,C13 (structure shown below) inhibits TRPM5, but also activates the Ca++ flux response (arrows).

Compound F001344,A3

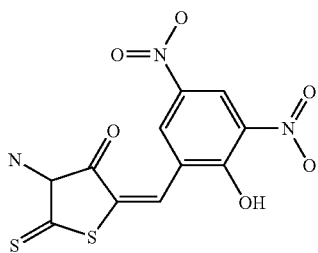

Compound F001348,C13

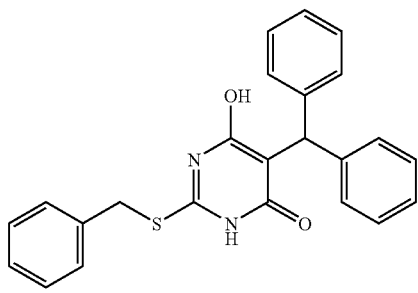

FIG. 9A shows FLIPR traces in a TRPM5 assay for 4 concentrations of a test compound, compound 1 (structure shown below). Panel 1 shows dose responsive inhibition of the TRPM5 response. Panels 2 and 3 demonstrate that increasing dose of the compound does not alter KCl or Ca++ responses. The quantitation of the these results is shown in FIG. 9B. Examples of two additional test compounds (compounds 2 and 3) are shown in FIG. 9C, which shows non-specific inhibition TPRM5, where compound 2 also inhibits the KCl response and compound 3 inhibits the Ca++ response.

Compound 1

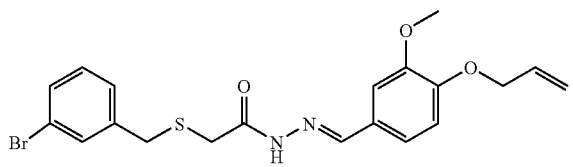

The KCl counterscreen is also useful for the identification of selective TRPM5 enhancing compounds. FIG. 10 shows the selective enhancement of TRPM5. The counterscreen experiments were performed as described above in the presence of test compound 4. TRPM5 expressing HEK and CHO cells demonstrated a 131% and 135% maximal stimulation upon addition of test compound 4, respectively. Addition of increasing amounts of test compound 4 also resulted in a dose-dependent increase in TRPM5 activity (FIG. 11). Furthermore, very strong enhancement is seen at suboptimal ($EC_{10}$) concentrations of ATP agonist using compound 5 (FIG. 12).

Example 5

High Throughput Assay Using a Dominant Negative TRPM5

Deletion mutants were generated to examine whether specificity for TRPM5 could be achieved using a dominant negative form of the channel. The N1000 deletion mutant is a form of mTRPM5 in which the first 1000 base pairs of the gene have been deleted and the N2000 deletion mutant contains a deletion of the first 2000 base pairs of the gene. The first 2000 base pairs of the gene correspond to the amino-terminal domain of the mTRPM5 ion channel. Deletion of this region results in a truncated version of the protein where the entire amino-terminal domain is removed and the protein begins with the first transmembrane region of the ion channel. The deletion mutants were constructed by PCR using primers designed to amplify the gene with the first 1000 base pairs deleted and the first 2000 base pairs deleted, respectively. The experiments described below were performed as previously described in terms of number of cells used, incubation times and dyes.

Experiments were performed by comparing transfection of different ratios of the deletion mutants to wildtype mTRPM5 as compared to the wildtype mTRPM5 with a null vector. The total amount of transfected DNA was kept constant at 4 μg. $1 \times 10^6$ HEK 293 cells were plated in 6 well dishes overnight. Ratios of deletion mutant mTRPM5/wildtype mTRPM5 and wildtype mTRPM5/pSV3-neo were then transfected into the HEK 293 cells using Lipofectamine 2000 as indicated in Table 1. One day following transfection, 15,000 cells/well were plated on 384 plates and maintained in an incubator overnight. The following day the cells were loaded with membrane potential dye at 37° C. and response to A23187 and carbachol dose responses were compared.

TABLE 1

Transfections in HEK 293 Cells Followed by TRPM5 Assay Experimental Design

| Wt-mTrpM5 | 3.8 μg | 3 μg | 2 μg | 1 μg | 0.2 μg | 4 μg |
|---|---|---|---|---|---|---|
| N1000 | 0.2 μg | 1 μg | 2 μg | 3 μg | 3.8 μg | 0 μg |
| Wt-mTrpM5 | 3.8 μg | 3 μg | 2 μg | 1 μg | 0.2 μg | 4 μg |
| pSV3-neo | 0.2 μg | 1 μg | 2 μg | 3 μg | 3.8 μg | 0 μg |

As shown in FIGS. 13A-13B, as the concentration of the deletion mutant increases, the relative fluorescence in response to A23187 (FIG. 13A) or carbachol (FIG. 13B) decreases. However, the decrease is absent in the presence of the null vector (pSV3-neo). In addition, there is no effect on the calcium response to the ligands, indicating that the decrease in the membrane potential response cannot be attributed to altering the calcium concentration.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All publications, patents and patent applications cited herein are incorporated by reference in their entirety into the disclosure.

What is claimed is:

1. A high throughput screening assay for identifying TRPM5 ion channel specific enhancers comprising:
   (a) determining an optimal and suboptimal concentration of an agent that increases intracellular calcium concentration in a cell, wherein the optimal concentration fully activates and the suboptimal concentration does not fully activate the TRPM5 ion channel;
   (b) contacting a cell expressing TRPM5 with a suboptimal concentration of an agent that increases intracellular calcium concentration, wherein the cell has been preloaded with a membrane potential fluorescent dye;
   (c) contacting the cell in step (b) with a potential enhancing compound;
   (d) using an optical detector, measuring the fluorescent intensity of the cell in step (b) in the presence of said potential enhancing compound; and
   (e) comparing the measured fluorescent intensity in step (d) to the fluorescent intensity of a different cell expressing TRPM5 in the presence of an optimal concentration of the agent from step (a), wherein a TRPM5 enhancer is a compound that increases TRPM5 activity in the cell in the presence of the suboptimal concentration of step (b).

2. The assay of claim 1, further comprising selecting one or more test compounds that enhance TRPM5 activity.

3. The assay of claim 1, wherein said cells are located in a multi-well vessel.

4. The assay of claim 3, wherein said multi-well vessel comprises up to 96 wells.

5. The assay of claim 3, wherein said multi-well vessel comprises greater than 96 wells.

6. The assay of claim 3, wherein said multi-well vessel comprises 384 wells.

7. The assay of claim 3, wherein said multi-well vessel comprises 1536 wells.

8. The assay of claim 1, wherein said agent that increases calcium concentration is selected from the group consisting of: thrombin, adenosine triphosphate (ATP), carbachol, calcium ionophores, and agonists of endogenous G protein coupled receptor molecules.

9. The assay of claim 8, wherein said agent is thrombin.

10. The assay of claim 8, wherein said agent is ATP.

11. The assay of claim 8, wherein said agent is carbachol.

12. The assay of claim 1, wherein said membrane potential fluorescent dye is a Fluorescent Imaging Plate Reader Membrane Potential (FMP) dye.

13. The assay of claim 1, wherein said optical detector is selected from the group consisting of: Fluorescent Imaging Plate Reader, FLEXStation, Voltage/Ion Probe Reader (VIPR), fluorescent microscope and charge-coupled device (CCD) camera, and Pathway HT.

14. The assay of claim 13, wherein said optical detector is a Fluorescent Imaging Plate Reader.

15. The assay of claim 1, wherein a TRPM5 specific enhancer increases TRPM5 activity relative to the activity of the TRPM5 ion channel in the presence of a suboptimal dose of the agent that increases intracellular calcium concentration.

16. The assay of claim 1, wherein said optical and suboptimal concentration in step (a) are determined experimentally.

17. The assay of claim 1, wherein the cell in step (a) is from the same population of cell from those in step (b).

* * * * *